(12) United States Patent
Dusselier et al.

(10) Patent No.: US 11,691,131 B2
(45) Date of Patent: Jul. 4, 2023

(54) METHODS TO PRODUCE ZEOLITES WITH THE GME TOPOLOGY AND COMPOSITIONS DERIVED THEREFROM

(71) Applicant: California Institute Of Technology, Pasadena, CA (US)

(72) Inventors: Michiel J. Dusselier, Kessel-Lo (BE); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 15 days.

(21) Appl. No.: 16/952,486

(22) Filed: Nov. 19, 2020

(65) Prior Publication Data

US 2021/0069682 A1  Mar. 11, 2021

Related U.S. Application Data

(62) Division of application No. 15/864,392, filed on Jan. 8, 2018, now Pat. No. 11,167,275, which is a division of application No. 15/050,839, filed on Feb. 23, 2016, now Pat. No. 9,878,312.

(60) Provisional application No. 62/133,074, filed on Mar. 13, 2015, provisional application No. 62/119,945, filed on Feb. 24, 2015.

(51) Int. Cl.
| | |
|---|---|
| *B01J 29/70* | (2006.01) |
| *B01J 29/04* | (2006.01) |
| *C01B 39/48* | (2006.01) |
| *B01D 53/86* | (2006.01) |
| *C07C 67/37* | (2006.01) |
| *C07C 29/48* | (2006.01) |
| *C07C 209/14* | (2006.01) |
| *C01B 39/06* | (2006.01) |
| *C07C 29/50* | (2006.01) |
| *C07C 1/20* | (2006.01) |
| *C10G 45/68* | (2006.01) |
| *C10G 3/00* | (2006.01) |
| *C10G 45/64* | (2006.01) |
| *C10G 50/00* | (2006.01) |
| *C10G 49/08* | (2006.01) |
| *C10G 47/20* | (2006.01) |
| *C01B 21/04* | (2006.01) |
| *C07C 7/13* | (2006.01) |
| *B01D 53/94* | (2006.01) |

(52) U.S. Cl.
CPC ........ B01J 29/048 (2013.01); B01D 53/8628 (2013.01); C01B 21/0411 (2013.01); C01B 39/06 (2013.01); C01B 39/48 (2013.01); C07C 1/20 (2013.01); C07C 7/13 (2013.01); C07C 29/48 (2013.01); C07C 29/50 (2013.01); C07C 67/37 (2013.01); C07C 209/14 (2013.01); C10G 3/49 (2013.01); C10G 45/64 (2013.01); C10G 45/68 (2013.01); C10G 47/20 (2013.01); C10G 49/08 (2013.01); C10G 50/00 (2013.01); *B01D 53/9418* (2013.01); *B01D 2251/2062* (2013.01); *B01D 2255/20792* (2013.01); *B01D 2255/50* (2013.01); *B01J 2229/186* (2013.01); *C07C 2521/12* (2013.01); *C07C 2523/06* (2013.01); *C07C 2529/70* (2013.01); *C10G 2300/1088* (2013.01); *C10G 2300/1096* (2013.01); *C10G 2400/22* (2013.01); *C10G 2400/30* (2013.01); *Y02C 20/10* (2013.01); *Y02C 20/30* (2013.01); *Y02P 20/52* (2015.11); *Y02P 30/20* (2015.11); *Y02P 30/40* (2015.11)

(58) Field of Classification Search
None
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 3,140,253 A | 7/1964 | Plank et al. |
| 3,904,738 A | 9/1975 | Robson |
| 4,061,717 A | 12/1977 | Kerr et al. |
| 4,503,024 A | 3/1985 | Bourgogne et al. |
| 4,544,538 A | 10/1985 | Zones |
| 5,283,047 A | 2/1994 | Vaughan et al. |
| 5,958,370 A | 9/1999 | Zones et al. |
| 6,086,848 A * | 7/2000 | Nakagawa ............ C01B 37/005 423/706 |
| 6,187,283 B1 | 2/2001 | Chiyoda et al. |

(Continued)

FOREIGN PATENT DOCUMENTS

| | | |
|---|---|---|
| EP | 1216960 A2 | 6/2002 |
| WO | 99/08961 A1 | 2/1999 |

(Continued)

OTHER PUBLICATIONS

Bleken, et al., "The Effect of Acid Strength on the Conversion of Methanol to Olefins Over Acidic Microporous Catalysts with the CHA Topology", Top. Catal. Jan. 2009, vol. 52, 218-228.

(Continued)

*Primary Examiner* — Yun Qian
(74) *Attorney, Agent, or Firm* — BakerHostetler

(57) ABSTRACT

The present disclosure is directed to microporous crystalline aluminosilicate structures with GME topologies having pores containing organic structure directing agents (OSDAs) comprising at least one piperidinium cation, the compositions useful for making these structures, and methods of using these structures. In some embodiments, the crystalline zeolite structures have a molar ratio of Si:Al that is greater than 3.5.

9 Claims, 8 Drawing Sheets

(56) References Cited

U.S. PATENT DOCUMENTS

| | | | |
|---|---|---|---|
| 6,423,295 B1* | 7/2002 | Huo | B01D 15/00 423/706 |
| 7,008,610 B2 | 3/2006 | Cao et al. | |
| 9,364,782 B1 | 6/2016 | Xie et al. | |
| 2002/0076376 A1 | 6/2002 | Huo | |
| 2002/0119887 A1 | 8/2002 | Huo et al. | |
| 2005/0154244 A1 | 7/2005 | Cao et al. | |
| 2005/0197519 A1 | 9/2005 | Cao et al. | |

FOREIGN PATENT DOCUMENTS

| | | |
|---|---|---|
| WO | 2005/063624 A1 | 7/2005 |
| WO | 2008/016423 A1 | 2/2008 |

OTHER PUBLICATIONS

Burton, et al., "Organic Molecules in Zeolite Synthesis: Their Preparation and Structure Directing Effects", In Stud. Surf. Sci. Catal., Elsevier: 2007; vol. 168, 37-179.

Cartlidge, et al. "Hydrothermally Stable Chabazites for the Selective Preparation of Olefins from Methanol", In Zeolites: Facts, Figures, Future, Jacobs, Eds. Elsevier: Amsterdam, 1989, 1151-1161.

Chen et al., "IR Spectroscopic Study of CD3CN Adsorbed on ALPO-18 Molecular Sieve and the Solid Acid Catalysts SAPO-18 and MeAPO-18", J. Chem. Soc., Jan. 1994, 90(22), 3455-3459.

Chen et al., "SAPO-18 Catalysts and Their Bronsted Acid Sites", J. Phys. Chem., Sep. 1994, 98, 10216-10224.

Chen, et al., "MAPO-18 (M=Mg, Zn, Co): A New Family of Catalysts for the Conversion of Methanol to Light Olefins", Chem. Soc., Chem. Commun., Jan. 1994, 603-604.

Chiyoda et al., "Hydrothermal Conversion of Y-Zeolite Using Alkaline-Earth Cations", Micro. and Meso. Mat., 1999, 32, 257-264.

Chiyoda, et al., "Adsorption Studies with gmelinite Zeolites Containing mono-, di- and tri-valent Cations", Microporous Mesoporous Mater., 2000, 38 (2-3), 143-149.

Daniels, et al., "Cationic Polymers as Templates in Zeolite Crystallization", J. Am. Chem. Soc., 1978, 100(10), 3097-3100.

Davis et al., "Synthesis of Gmelinite and ZSM-12 Zeolites with a Polymer Template", J. Chem. Soc., 1988, 920-921.

Davis, et al., "Zeolite and Molecular Sieve Synthesis", Chem. Mater., 1992, vol. vol. 4, 756-768.

Dusselier et al., "Influence of Organic Structure Directing Agent Isomer Distribution on the Synthesis of SSZ-39," Chemistry of Materials, Mar. 30, 2015, vol. 27, 2695-2702.

Froment, et al., In Catalysis in the Conversion of Methanol into Olefin, Spivey, J. J., Ed. The Royal Society of Chemistry, 1992, vol. 9(1), 64 pgs.

Hunsicker et al., "Framework Zinc-Substituted Zeolites: Synthesis, and Core-Level and Valence-Band XPS", Chem. Mater., Oct. 8, 2002, 14, 4807-4811.

Ji, et al., "Organic-Free Synthesis of CHA-Type Zeolite Catalysts for the Methanol-to-Olefins Reaction", ACS Catalysis, 2015, vol. 5, 4456-4465.

Martin, et al., "Efficient Synthesis of the Cu-SSZ-39 Catalyst for DeNOx Applications (Electronic Supplementary Information)" Royal Society of Chemistry Journal, 2015, 10 pgs.

Martin, et al., "Efficient Synthesis of the Cu-SSZ-39 Catalyst for DeNOxApplications", Royal Society of Chemistry Journal, Jan. 2012, 4 pgs.

Moliner, et al., "Cu-SSZ-39, an Active and Hydrothermally Stable Catalyst for the Selective Catalytic Reduction of NOx", Chem. Commun., 2012, 48(66), 8264-8266.

Olsbye, et al., "Conversion of Methanol to Hydrocarbons: How Zeolite Cavity and Pore Size Controls Product Selectivity", Angew. Chem. Int. Ed., Apr. 2012, vol. 51(24), 5810-5831.

Ren, et al., Designed Copper-Amine Complex as an Efficient Template for One-Pot Synthesis of Cu-SSZ-13 Zeolite with Excellent Activity for Selective Catalytic Reduction of NOxbY NH/, Chem Commun., May 2011, 47, 9789-9791.

Tsuda et al., "Catalytic Hydrogenation of Dimethylpyridine Methiodides and Stereochemistry of Hydrogenation Products," Chemical and Pharmaceutical Bulletin, 1970, vol. 18(12), 2499-2506.

Tsuiji, et al., "Synthesis of 4,4'-trimethylenebis(1-benzyl-1-methylpiperidinium) diastereomers and their use as structure-directing agents in pure-silica molecular sieve syntheses", Microporous and Mesoporous Materials, 28(3), May 1999, 519-530.

Vermeiren, et al., "Impact of Zeolites on the Petroleum and Petrochemical Industry", Top. Catal. 2009, 52(9), 1131-1161.

Wagner, et al., "Guest/Host Relationships in the Synthesis of the Novel Cage-Based Zeolites SSZ-35, SSZ-36, and SSZ-39", J. Am. Chem. Soc., Dec. 1999, 122,263-273.

Wang, et al., "Dealumination of Zeolites—II. Kinetic Study of the Dealumination by Hydrothermal Treatment of a NH4NaY Zeolite", J. Catal., Aug. 19, 1991, vol. 130(2), 459-470.

Wu et al., "Mesoporous SSZ-13 Zeolite Prepared by a Dual-Template Method with Improved Performance in the Methanol-to-Olefins Reaction", J. Catal., Feb. 2013, vol. 298, 27-40.

Yuen, et al., "Product Selectivity in Methanol to Hydrocarbon Conversion for Isostructural Compositions of AFI and CHA Molecular Sieves", Microporous Mater., Feb. 1994, 2(2), 105-117.

Zones et al., "Searching for New High Silica Zeolites Through a Synergy of Organic Templates and Novel Inorganic Conditions", Micro and Meso Mat., 1998, 199-211.

* cited by examiner

METHODS TO PRODUCE ZEOLITES WITH THE GME TOPOLOGY AND COMPOSITIONS DERIVED THEREFROM

CROSS REFERENCE TO RELATED APPLICATIONS

This application is a divisional application to U.S. patent application Ser. No. 15/864,392, filed Jan. 8, 2018, which is a divisional application to U.S. patent application Ser. No. 15/050,839, filed Feb. 23, 2016, which issued as U.S. Pat. No. 9,878,312 on Jan. 30, 2018, which itself claims priority to U.S. Patent Application Ser. No. 62/119,945 filed Feb. 24, 2015 and U.S. Patent Application Ser. No. 62/133,074 filed Mar. 13, 2015, the contents of all of which are incorporated by reference herein in their entireties for all purposes.

TECHNICAL FIELD

The present disclosure is directed to producing zeolite structures with GME topologies using organic structure directing agents (OSDAs), and the compositions and structures resulting from these methods.

BACKGROUND

The GME topology describes a microporous molecular sieve having 1D 12-membered ring (MR) channels intersected by 8 MR channels in 2 dimensions. Its 3D channel (12×8×8) system with pore sizes of 7.11×7.11 Å (12MR) and 3.41×3.41 Å (8MR), respectively, can include spheres up to 7.76 Å. This framework was first recognized in the natural occurring aluminosilicate (zeolite) mineral gmelinite. Since then, routes towards synthetic GME have been explored. Two notable paths are known from the literature: one using cationic (DABCO) polymeric templates in conjunction with a silica sol and sodium aluminate as respective Si and Al sources, and one based on the hydrothermal conversion of zeolite Y (FAU) in presence of $Sr^{2+}$ cations. However, most materials, and especially the natural occurring gmelinite, are faulted (containing crystallographic errors in the structure, possible causing obstructions of channels etc.) and therefore possess rather low sorption capacities. When exchanged with sodium, nitrogen adsorption capacities, as measured by $N_2$-physisorption at −196° C., were reported to be nearly 0 $cm^3 \cdot g^{-1}$ for natural Na-GME and respectively 0.055 $cm^3 \cdot g^{-1}$ and 0.031 $cm^3 \cdot g^{-1}$ for the DABCO-GME and the GME made by converting FAU. This, together with streaking in electron diffraction indicated that these samples are all highly faulted. It is moreover known that this can be caused by an intergrowth of chabazite (framework topology CHA). The degree of faulting (although present in lesser extent in the DABCO-GME) largely determines the sorption capacity as it blocks the large 12MR channels.

It would be desirable to find a synthetic route to GME with an organic structure directing agent (SDA), that prevents CHA intergrowth and stacking faults and in general, it would be desirable to find a route with a simpler SDA, as the 'polymeric DABCO' OSDA is hard to obtain. It would be also be beneficial to find a synthetic route towards GME with Si/Al values above 3.5, since this parameter largely influences the sorption and catalytic properties and the (hydrothermal) stability of the framework.

The present invention is directed to addressing at least some of the shortcomings of the existing art.

SUMMARY

The present invention is directed to the use of quaternary piperidinium salts to prepare zeolites having GME topologies, and the novel materials derived from these processes.

The disclosure provided certain embodiments directed to processes of making zeolite compositions of a GME topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a mineralizing agent; and (d) an organic structure directing agent (OSDA) comprising at least one isomer of the quaternary piperidinium cation of Formula (I):

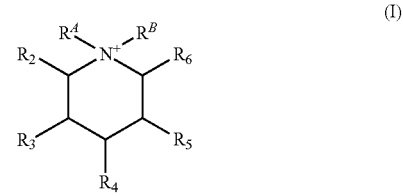

(I)

under conditions effective to crystallize a crystalline microporous solid of GME topology;

wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In certain aspects of this disclosure, the process is done in the absence of the sources of aluminum oxide, boron oxide, gallium oxide, hafnium oxide, iron oxide, tin oxide, titanium oxide, indium oxide, vanadium oxide, zirconium oxide, or combination or mixture thereof. In other embodiments, the process comprises hydrothermal treating of an aqueous composition comprising (a) a source of a silicon oxide; (b) a source of aluminum oxide; (c) mineralizing agent, preferably a hydroxide; and (d) the organic structure directing agent (OSDA) of Formula (I).

The quaternary piperidinium cation of Formula (I) is also defined in various embodiments in terms of sub-genera and specific quaternary piperidinium cations. For example, in some embodiments, the quaternary piperidinium cation is defined in terms of:

(a) structures of Formula (IA) or (IB):

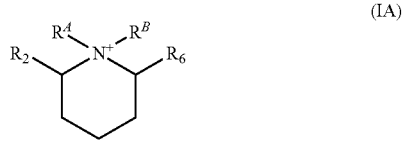

(IA)

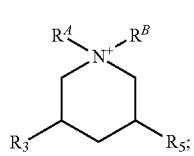

(b) certain N,N-dialkyl-2,6-lupetidinium cations or an N,N-dialkyl-3,5-lupetidinium cations:

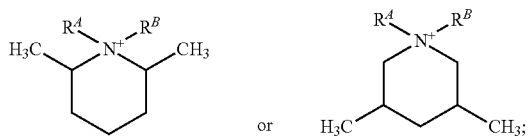

(c) cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof; and (d) cis-N,N-dimethyl-3,5-lupetidinium cation, trans-N,N-dimethyl-3,5-lupetidinium cation, cis-N,N-dimethyl-2,6-lupetidinium cation, trans-N,N-dimethyl-2,6-lupetidinium cation or a combination thereof.

In general, the quaternary 3,5 piperidinium cations, or mixtures comprising these cations are preferred, particularly, cis-N,N-dialkyl-3,5-lupetidinium cation, or cis-N,N-dimethyl-3,5-lupetidinium cation, of mixtures comprising these cations.

The nature of the sources of the various oxides and their ratio ranges, the nature of the mineralizing agent, and the hydrothermal heating conditions are also disclosed as separate embodiments.

In some embodiments, the processes further comprise isolating the crystalline microporous solid of GME topology and on some cases, further processing the isolated crystalline solids. These processes include process steps to remove at least a portion and preferably substantially all of the OSDA occluded in the pores of the isolated solids. In some embodiments, this further processing is done in the presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In other embodiments, the further processing is done in the absence of such salts. In other aspects, these salts are added in a separate step from the removal of the OSDA.

These compositions typically include analogous embodiments as described for the process that more specifically define the nature of the OSDA, the ratios of the various components, and the processing conditions. Still other embodiments provide for crystalline microporous solids having pores at least some of which are occluded with at least one isomer of the quaternary piperidinium cation of Formula (I).

The products of the hydrothermal treating may be isolated and subjected to one or more of further processing conditions. Such treatments include:

(a) contacting the isolated crystalline microporous solid with ozone or other oxidizing agent at a temperature in a range of 100° C. to 200° C.; and (b) heating the isolated crystalline microporous solid at a temperature in a range of from about 200° C. to about 600° C. in either the absence or presence of an alkali, alkaline earth, transition metal, rare earth metal, ammonium or alkylammonium salts;

in each case for a time sufficient to form a dehydrated or an OSDA-depleted crystalline microporous product. Certain sub-embodiments describe specific aspects of these treatments.

These dehydrated or OSDA-depleted crystalline microporous products may be further treated with an aqueous ammonium or metal cation salt and/or with at least one type of transition metal or transition metal oxide.

Various embodiments disclose the compositions prepared by any one of the processes embodiments. These include compositions which may be described as:

(a) compositions comprising the aqueous compositions used in the hydrothermal treatments together with a compositionally consistent crystalline microporous aluminosilicate product, the compositionally consistent crystalline microporous products containing the OSDA used in their preparation occluded in their pores;

(b) the isolated crystalline microporous products which contain the of Formula (I) occluded in their pores; and (c) the crystalline microporous products which have been dehydrated or from which the OSDAs have been substantially depleted from their pores and/or which have been post-treated to add salts, metals, or metal oxides into the pores of the crystalline microporous products.

While these compositions have been described and claimed in terms of the processes used to prepare them, other embodiments describe and claim these compositions in terms which do not require these process limitations. For example, certain embodiments disclose compositions of crystalline microporous solids of GME topology, described in terms of the ratios of the respective components. For example, in certain embodiments, the crystalline microporous solids, whether containing the OSDA or not, have molar ratio of Si:Al of from greater than 3.5 to about 15 (or $SiO_2/Al_2O_3$ ratio greater than 7 to about 30). Independent embodiments provide subsets of these ranges.

In other embodiments, the crystalline microporous solids are described in terms of certain physical characteristics of the aluminosilicate solids, for example with respect to XRD patterns, $^{29}Si$ MAS NMR spectra, $^{27}Al$ MAS NMR spectra, $N_2$ or argon physisorption isotherms, and thermogravimetric analysis (TGA) data.

Still other embodiments include those which use the disclose compositions in an array of catalytic processes.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings.

DETAILED DESCRIPTION OF ILLUSTRATIVE EMBODIMENTS

The present invention is directed to methods of producing crystalline aluminosilicate molecular sieves with the GME topology using quaternary piperidine OSDAs and the corresponding compositions. Additionally, new GME aluminosilicate compositions, called CIT-9, are disclosed, with molar ratios of Si:Al that are greater than 3.5. The new synthesis routes give access to GME zeolites with pore volumes over 0.1 cm$^3$/g.

Figure 1:
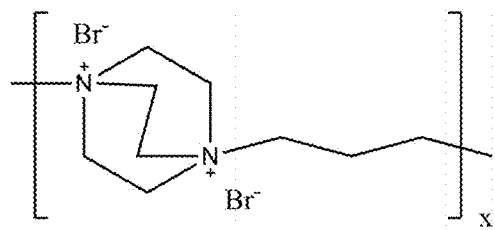
FIG. 1 shows the DABCO polymer, previously the only known OSDA for synthetic GME zeolite synthesis.

The only successful OSDA reported so far in the preparation of GME materials is the DABCO polymer, structurally illustrated in FIG. 1. Moreover, all synthetic GMEs prepared so far have a molar ratio of Si:Al ratio in the range of from 2.0-3.5. GME with Si:Al ratios above 3.5 are desirable, since this ratio largely influences the sorption and catalytic properties and the (hydrothermal) stability of the framework.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement.

Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) of a process is the ability to provide the named GME compositions using the named OSDAs under conditions favoring the stabile formation of the GME compositions, without the necessary need for other ingredients, even if other such components are present.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Unless otherwise stated, ratios or percentages are intended to refer to mole percent or atom percent, as appropriate.

Throughout this specification, words are to be afforded their normal meaning, as would be understood by those skilled in the relevant art. However, so as to avoid misunderstanding, the meanings of certain terms will be specifically defined or clarified.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

The terms "oxygenated hydrocarbons" or "oxygenates" as known in the art of hydrocarbon processing to refer to components which include alcohols, aldehydes, carboxylic acids, ethers, and/or ketones which are known to be present in hydrocarbon streams or biomass streams from other sources (e.g., ethanol from fermenting sugar).

The terms "separating" or "separated" carry their ordinary meaning as would be understood by the skilled artisan, insofar as they connote physically partitioning or isolating the product material from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though it is preferred.

Unless otherwise indicated, the term "isolated" means physically separated from the other components so as to be free of at least solvents or other impurities, such as starting materials, co-products, or byproducts. In some embodiments, the isolated crystalline materials, for example, may be considered isolated when separated from the reaction mixture giving rise to their preparation, from mixed phase co-products, or both. In some of these embodiments, for example, pure aluminosilicates (or structures containing incorporated OSDAs) can be made directly from the described methods. In some cases, it may not be possible to separate crystalline phases from one another, in which case, the term "isolated" can refer to separation from their source compositions.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "method(s)" and "process(es)" are considered interchangeable within this disclosure.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. These rings are not necessarily symmetrical, due to a variety of effects including strain induced by the bonding between units that are needed to produce the overall structure, or coordination of some of the oxygen atoms of the rings to cations within the structure. The term "silicate" refers to any composition including silicate (or silicon oxide) within its framework. It is a general term encompassing, for example, pure-silicate (i.e., absent other detectable metal oxides within the framework), aluminosilicate, borosilicate, or titanosilicate structures. The term "aluminosilicate" refers to any composition including silicon and aluminum oxides within its framework. In some cases, either of these oxides may be substituted with other oxides. "Pure aluminosilicates" are those structures having no detectable other metal oxides in the framework. As long as the framework contains silicon and aluminum oxides, these substituted derivatives fall under the umbrella of aluminosilicates. The term "zeolite" also refers to an aluminosilicate composition that is a member of this family. When described as "optionally substituted," the zeolite framework may contain boron, gallium, hafnium, iron, tin, titanium, indium, vanadium, or zirconium atoms substituted for one or more aluminum or silicon atoms in the framework. As described elsewhere, the GME topology describes a microporous molecular sieve having 1D 12-membered ring (MR) channels intersected by 8 MR channels in 2 dimensions. Its 3D channel (12×8×8) system with pore sizes of 7.11×7.11 Å (12MR) and 3.41×3.41 Å (8MR), respectively, can include spheres up to 7.76 Å.

The material described herein as "CIT-9" refers to an crystalline microporous aluminosilicate material having a structure characteristics the same as a material produced by the OSDA route described herein, in which the OSDA comprises a cis-N,N-dimethyl-3,5-lupetidinium cation.

The present disclosure describes and is intended to lay claim to methods of making crystalline compositions, the compositions themselves, and methods of using the crystalline aluminosilicate compositions having a GME framework. As described elsewhere as well, it should be appreciated that any embodied feature described for one of these categories (i.e., compositions and methods of making or using) is applicable to all other categories.

Processes of Preparing Crystalline Compositions

Certain embodiments involve those process for preparing an aluminosilicate composition having a GME topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a mineralizing agent; and (d) an organic structure directing agent (OSDA) comprising at least one isomer of the quaternary piperidinium cation of Formula (I):

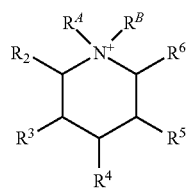
(I)

under conditions effective to crystallize a crystalline microporous aluminosilicate solid of GME topology; wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

The counterion to the cationic organic structure directing agent mixture in Formula (I) is generally a bromide, chloride, fluoride, iodide, or hydroxide ion, but the OSDA may be added also to the composition as an acetate, nitrate, or sulfate. In some embodiments, the quaternary piperidinium cation has an associated fluoride or hydroxide ion preferably substantially free of other halide counterions. In separate embodiments, the associated anion is hydroxide.

It should be appreciated that the instant invention provides that the quaternary piperidinium cation may comprise one or more stereoisomers of the same structural compound or two or more different compounds, selected from these options. For the sake of brevity, reference to an isomer by individual digits is intended to refer to that isomer substituted in that position. For example, the "2,6 isomer" refers to an isomer containing an alkyl substituent only in the $R^2$ and $R^6$ positions; a "3,5 isomer" refers to an isomer containing an alkyl substituent only in the $R^3$ and $R^5$ positions.

Reference to "isomers" in Formula (I) (and Formula (IA) and (IB) discussed elsewhere) refers to both structural and stereochemical isomers of the quaternary piperidinium cation. That is, reference to two or more isomers may encompass multiple structural isomers (e.g., individual mono-alkyl compounds substituted in the 2, 3, 4, 5, or 6 positions, or di-alkyl compounds substituted in the 2,3 and 2,4 and 2,5 and 2,6, and 3,4 and 3,5, and 4,5 positions, or combinations thereof). In some cases, these may include mixtures of homologs (e.g., where $R^2$ is methyl and $R^6$ is ethyl), stereoisomers of the same structural isomer (e.g., cis-2-methyl/6-methyl and trans-2-methyl/6-methyl), or combinations of both (e.g., cis-3-methyl/5-methyl and trans-3-methyl/5-ethyl).

For example, referring to the structure of Formula (I), options for the quaternary piperidinium cations include those where $R^2$, $R^3$, $R^4$, $R^5$, and $R^6$ are individually and independently methyl, ethyl, n-propyl, or iso-propyl, independent of stereochemistry. In separate embodiments, the carbon skeleton of piperidinium cation may be di-, tri-, tetra-, or penta-substituted with any of these $C_{1-3}$ alkyl groups, independent of stereochemistry.

The piperidine frameworks which derive the quaternary piperidinium cations may be conveniently derived from the products of hydrogenation of di-, tri, or tetraalkyl pyridine precursors, via the intermediary formation of the corresponding di-, tri, or tetraalkyl piperidinium precursors, for example using $Pt/H_2$ or Raney Nickel catalysts. Given the availability of such pyridine precursors, in some embodiments, dialkyl piperidinium frameworks are conveniently obtained by such processes, especially, for example, where $R^3$ and $R^5$ are alkyl, preferably ethyl or methyl, more preferably methyl or where $R^2$ and $R^6$ are alkyl, preferably ethyl or methyl, more preferably methyl. In the former case, where $R^3$ and $R^5$ are methyl and $R^2$, $R^4$, and $R^6$ are H, the structures are known as 3,5-lupetidinium cations. In the latter case, where $R^2$ and $R^6$ are methyl and $R^3$, $R^4$, and $R^5$ are H, the structures are known as 2,6-lupetidinium cations.

$R^A$ and $R^B$ are defined as being independently a $C_{1-3}$ alkyl, or together with the N to which they are bound form a 5 or 6 membered saturated or unsaturated ring. As such, in some embodiments, $R^A$ and $R^B$ are independently methyl, ethyl, n-propyl, or iso-propyl. In other embodiments, $R^A$ and $R^B$, together with the N to which they are bound, form a 5 or 6 membered saturated or unsaturated ring. For example, these may include structures described as a spiro-pyrrolidinium moiety, also described as a 5-azonia-spiro [4,5] decane:

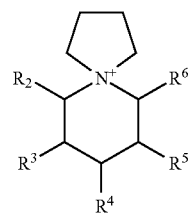

or a spiro-piperidinium moiety, also described as a 6-azonia-spiro [4,5] undecane:

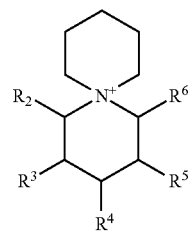

or a spiro-2,5-dihydro-1H-pyrrolium moiety, also described as a 5-azonia-spiro [4,5] dec-2-ene:

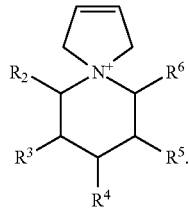

Again, in certain embodiments of these structures, the 2,6 positions (i.e., $R^2$ and $R^6$) are alkyl, preferably ethyl or methyl, more preferably methyl, the remaining positions being H. In other embodiments, the 3,5 positions (i.e., $R^3$ and $R^5$) are alkyl, preferably ethyl or methyl, more preferably methyl, the remaining positions being H.

In some embodiments, the OSDA used in these processes comprises at least one isomer of the quaternary piperidinium cation of Formula (IA) or (IB):

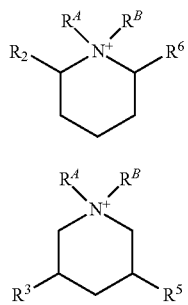

wherein $R^2$ $R^3$, $R^5$, and $R^6$ are independently $C_{1-3}$ alkyl.

In some embodiments, the quaternary piperidinium cation of Formula (I) is or comprises an N,N-dialkyl-2,6-lupetidinium cation or an N,N-dialkyl-3,5-lupetidinium cation:

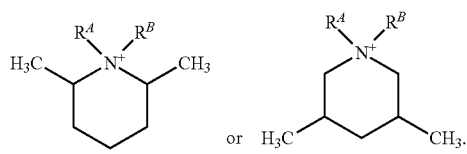

where $R^A$ and $R^B$ are $C_{1-3}$ alkyl, preferable methyl. In separate independent embodiments, the quaternary piperidinium cation of Formula (I) is or comprises an N,N-dialkyl-2,6-lupetidinium cation or an N,N-dialkyl-3,5-lupetidinium cation.

In related embodiments, the quaternary piperidinium cation of Formula (I) is an N,N-dimethyl-3,5-lupetidinium cation, N,N-dimethyl-2,6-lupetidinium cation, N,N-diethyl-3,5-lupetidinium cation, N,N-diethyl-2,6-lupetidinium cation, a 6,10-dimethyl-5-azonia-spiro[4.5]decane, a 1,5-dimethyl-6-azonia-spiro[5.5]undecane, a 7,9-dimethyl-5-azonia-spiro[4.5]decane, a 2,4-dimethyl-6-azonia-spiro[5.5]undecane, or a combination thereof.

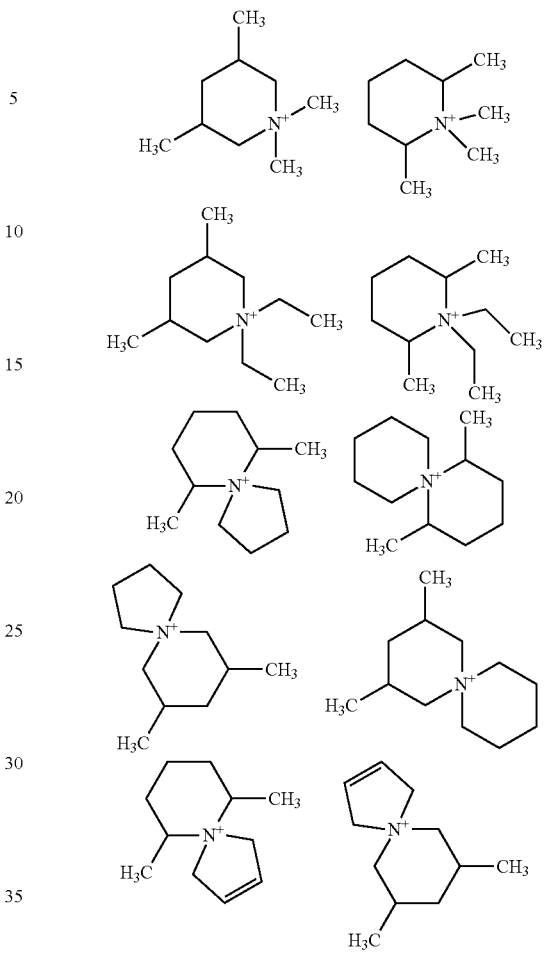

Still further embodiments include those where the quaternary piperidinium cation of Formula (I) is or comprises cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

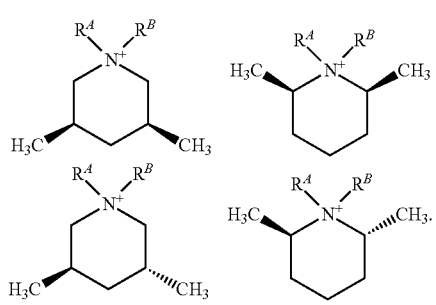

Including those wherein $R^{A'}$ and $R^B$ are both methyl.

In other embodiments, the quaternary piperidinium cation of Formula (I) comprise a mixture of cis-N,N-dimethyl-3,5-lupetidinium cation and trans-N,N-dimethyl-3,5-lupetidinium cation, a mixture of cis-N,N-dimethyl-2,6-lupetidinium cation and cis-N,N-dimethyl-3,5-lupetidinium cation, or a combination thereof.

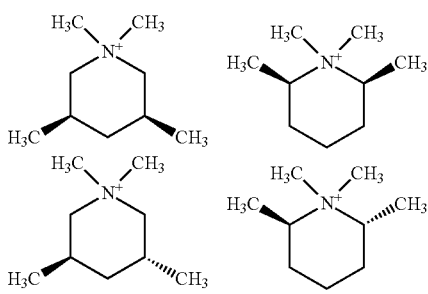

In some embodiments, the ratios of cis and trans in these di-substituted materials may range from about 99% cis/1% trans to about 0% cis/100% trans. In other embodiments, the at least two isomers of the quaternary piperidinium cation of Formula (I) comprise a mixture of cis-N,N-dimethyl-3,5-lupetidinium cation and trans-N,N-dimethyl-3,5-lupetidinium cation in a mole ratio of about 99% cis/1% trans to about 0% cis/100% trans. Other embodiments provide that these ratios range from about 98:2 to 95:5, from about 95:5 to 90:10, from 90:10 to 80:20, from 80:20 to 70:30, from 70:30 to 60:40, from 60:40 to 50:50, 50:50 to 40:60, from 40:60 to 30:70, from 30:70 to 20:80, from 20:80 to 10:90, from 10:90 to 0:100, from 95:5 to 75:25, from 75:25 to 50:50, from 50:50 to 25:75, from 25:75 to 5:100, or any combination of two or more of these ranges, including overlapping ranges, for example from 90:10 to 75:25. In each case, the ratios are mole % cis/mol % trans. As described elsewhere, cis-N,N-dimethyl-3,5-lupetidinium cations, or mixtures containing predominantly cis-N,N-dimethyl-3,5-lupetidinium cations are preferred.

As described above, the hydrothermal processes for preparing the crystalline microporous aluminosilicate solid of GME topology requires, inter alia:

(a) a source of a silicon oxide, and optionally a source of germanium oxide or combination thereof and (b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof.

In certain embodiments, the process is done in the absence of the source of aluminum oxide, boron oxide, gallium oxide, hafnium oxide, iron oxide, tin oxide, titanium oxide, indium oxide, vanadium oxide, zirconium oxide, or combination or mixture thereof.

In certain embodiments, the composition is absent any source of one or more of boron oxide, gallium oxide, germanium oxide, hafnium oxide, iron oxide, tin oxide, titanium oxide, indium oxide, vanadium oxide, or zirconium oxide.

In some embodiments, the sources of aluminum oxide, silicon oxide, or optional source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, mixed metal oxide, or combination thereof.

The processes are described thus far in terms of "a source of a silicon oxide, and optionally a source of germanium oxide or combination thereof" The use of a source of silicon oxide, germanium oxide, and any combination thereof represent individual and independent embodiments. The presence of a source of silicon oxide, either by itself or in combination with sources of germanium oxide is preferred.

The source of silicon oxide may comprise an aluminosilicate, a silicate, silica hydrogel, amorphous silica, silicic acid, fumed silica, colloidal silica, tetra-alkyl orthosilicate, a silica hydroxide, silicon alkoxide, or combination thereof. Sodium silicate or tetraorthosilicates are preferred sources. Corresponding sources of germanium oxide can include alkali metal orthogermanates, $M_4GeO_4$, containing discrete $GeO_4^{4-}$ ions, $GeO(OH)_3^-$, $GeO_2(OH)_2^{2-}$, $[(Ge(OH)_4)_8(OH)_3]^{3-}$ or neutral solutions of germanium dioxide contain $Ge(OH)_4$, or alkoxide or carboxylate derivatives thereof.

The source of aluminum oxide is or comprises an alkoxide, hydroxide, or oxide of aluminum, a sodium aluminate, an aluminum siloxide, an aluminosilicate, or combination thereof. In some embodiments, a mesoporous or zeolite aluminosilicate material may be used as a source of both aluminum oxide and silicon oxide. For example, FAU type zeolites serve as useful precursors, for example in structures having Si/Al=2.6 or higher In the presence of appropriate starting materials, the resulting crystalline compositions have the GME framework topology formed by these processes. In some cases, these may be characterized as a zeolite CIT-9 material.

Thus far, the processes (and associated compositions) have been described as in terms of the use or presence of a mineralizing agent Such a mineralizing agent typically comprises an aqueous hydroxide derived from an alkali metal or alkaline earth metal hydroxide, thereby rendering these compositions alkaline. In certain aspects of this embodiment, the alkali metal or alkaline earth metal hydroxide, may include, for example, LiOH, NaOH, KOH, RbOH, CsOH, $Mg(OH)_2$, $Ca(OH)_2$, $Sr(OH)_2$, or $Ba(OH)_2$. LiOH, NaOH, or KOH appear to be preferred. In some cases, the pH of the water is in a range of from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, or higher, or any combination of two or more of these ranges, for example, at least 11. Under these conditions, the oxide precursors can be expected to be at least partially hydrated or hydrolyzed to their hydroxide forms.

The processes and compositions may also be defined in terms of the ratios of the individual ingredients. In certain embodiments, the molar ratio of Al:Si is in a range of 0.0067 to 0.5 (or the molar ratio of Si:Al is in a range of from 2 to 150). In certain specific embodiments, the molar ratio of Al:Si is in a range of from 0.0067 to 0.008, from 0.008 to 0.01, from 0.01 to 0.02, from 0.02 to 0.03, from 0.03 to 0.04, from 0.04 to 0.05, from 0.05 to 0.1, from 0.1 to 0.11, from 0.11 to 0.12, from 0.12 to 0.13, from 0.13 to 0.14, from 0.14 to 0.15, from 0.15 to 0.16, from 0.16 to 0.17, from 0.17 to 0.18, from 0.18 to 0.2, from 0.2 to 0.22, from 0.22 to 0.24, from 0.24 to 0.26, from 0.26 to 0.28, from 0.28 to 0.3, from 0.3 to 0.32, from 0.32 to 0.34, from 0.34 to 0.36, from 0.36 to 0.38, from 0.38 to 0.4, from 0.4 to 0.42, from 0.42 to 0.44, from 0.44 to 0.46, from 0.46 to 0.48, from 0.48 to 0.5, or any combination of two or more of these ranges, for example from 0.01 to 0.5, or from 0.05 to 0.15. It should be appreciated that while these stoichiometries are defined solely in terms of Si and Al, some portion or all of the Si content may be substituted by Ge, and some portion of the Al may be substituted by B, Ga, Hf, Fe, Sn, Ti, In, V, or Zr.

In certain embodiments, the molar ratio of the respective OSDA:Si is in a range of 0.01 to 0.75. In certain specific, the molar ratio of OSDA:Si is in a range of from 0.01 to 0.02, from 0.02 to 0.03, from 0.03 to 0.04, from 0.04 to 0.05, from 0.05 to 0.1, from 0.1 to 0.11, from 0.11 to 0.12, from 0.12 to 0.13, from 0.13 to 0.14, from 0.14 to 0.15, from 0.15 to 0.16, from 0.16 to 0.17, from 0.17 to 0.18, from 0.18 to 0.2, from 0.2 to 0.22, from 0.22 to 0.24, from 0.24 to 0.26, from 0.26 to 0.28, from 0.28 to 0.3, from 0.3 to 0.32, from 0.32 to 0.34, from 0.34 to 0.36, from 0.36 to 0.38, from 0.38 to 0.4, from 0.4 to 0.42, from 0.42 to 0.44, from 0.44 to 0.46, from 0.46 to 0.48, from 0.48 to 0.5, from 0.5 to 0.55, from 0.55 to 0.6, from 0.6 to 0.65, from 0.65 to 0.7, from 0.7 to 0.75, or any combination of two or more of these ranges, for example from 0.01 to 0.5, or from 0.1 to 0.5. Again, while described in terms of Si alone, in additional embodiments, the reference to Si may also refer to the presence of Si, Ge, or both, such that the named proportion of Si refers to the combined amounts of Si and Ge.

In other embodiments, the molar ratio of water:Si is in a range of 5 to 50. In certain specific embodiments, the molar ratio of water:Si is in a range of from 5 to 6, from 6 to 7, from 7 to 8, from 8 to 9, from 9 to 10, from 10 to 11, from 11 to 12, from 12 to 13, from 13 to 14, from 14 to 15, from 15 to 16, from 16 to 17, from 17 to 18, from 18 to 19, from 19 to 20, from 20 to 22, from 22 to 24, from 24 to 26, from 26 to 28, from 28 to 30, from 30 to 32, from 32 to 34, from 34 to 36, from 36 to 38, from 38 to 40, from 40 to 42, from 42 to 44, from 44 to 46, from 46 to 48, from 48 to 50, or any combination of two or more of these ranges, for example from 10 to 50 or from 10 to 25. Again, while these ratios are described in terms of Si alone, in additional embodiments, these ratios may also refer to the presence of Si, Ge, or both, such that the named proportion of Si refers to the combined amounts of Si and Ge.

In other embodiments, the molar ratio of total hydroxide:Si is in a range of 0.1 to 1.25. As used herein, the term "total hydroxide" includes the amount of hydroxide introduced with the OSDA and separately added, for example as the mineralizer or other sources. In certain specific embodiments, the molar ratio of water:Si is in a range of from 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.6, from 0.6 to 0.65, from 0.65 to 0.7, from 0.7 to 0.75, from 0.75 to 0.8, from 0.8 to 0.85, from 0.85 to 0.9, from 0.9 to 0.95, from 0.95 to 1, from 1 to 1.05, from 1.05 to 1.1, from 1.1 to 1.15, from 1.15 to 1.2, from 1.2 to 1.25, or any combination of two or more of these ranges, for example from 0.4 to 1. Again, while these ratios are described in terms of Si alone, in additional embodiments, these ratios may also refer to the presence of Si, Ge, or both, such that the named proportion of Si refers to the combined amounts of Si and Ge.

The hydrothermal treating is typically done at a temperature in a range of from about 100° C. to about 200° C. for a time effective for crystallizing the respective crystalline microporous aluminosilicate solid. Independent embodiments include those where the hydrothermal treating is done at at least one temperature in a range of from about 100° C. to 120° C., from 120° C. to 140° C., from 140° C. to 160° C., from 160° C. to 180° C., from 180° C. to 200° C., or any combination of two or more of these ranges. In certain specific embodiments, the temperature is in a range of from 120° C. to 180° C. These ranges provide for convenient reaction times, though higher and lower temperatures may also be employed. In some embodiment, these temperatures are applied for times in a range of from 1 hour to 14 days. In certain embodiments, the temperature is applied for time in a range of 1 to 6 hour, from 6 to 12 hours, from 12 to 24 hours, from 24 to 48 hours, from 2 to 4 days, from 4 to 8 days, from 8 to 14 days, or any combinations of two or more of these ranges, for example, from 12 to 48 hours. Again, longer or shorter times may also be employed. This hydrothermal treating is also typically done in a sealed autoclave, at autogenous pressures. Some exemplary reaction conditions are provided in the Examples.

Once the initial aluminosilicate solids are prepared, the processes include embodiments further comprising isolating these solids. These crystalline solids may be removed from the reaction mixtures by any suitable means (e.g., filtration, centrifugation, etc.), washed, and dried. Such drying may be done in air at temperatures ranging from 25° C. to about 200° C. Typically, such drying is done at a temperature of about 100° C.

These crystalline microporous aluminosilicate solids may be further modified, for example, by incorporating metals with the pore structures, either before or after drying, for example by replacing some of the cations in the structures with additional metal cations using techniques known to be suitable for this purpose (e.g., ion exchange). Such cations can include those of rare earth, Group 1, Group 2 and Group 8 metals, for example Li, Na, K, Ca, Cd, Co, Cu, Fe, Mg, Mn, Ni, Pt, Pd, Re, Sn, Ti, V, W, Zn and their mixtures.

The isolated aluminosilicate products may be subject to further processing, such further comprising heating the isolated crystalline microporous solid at a temperature in a range of from about 250° C. to about 550° C. to form an OSDA-depleted product. The heating is done in an oxidizing atmosphere, such as air or oxygen, or in the presence of other oxidizing agents. In other embodiments, the heating is done in an inert atmosphere, such as argon or nitrogen.

In those embodiments where the processing involved heating, typical heating rates include is 0.1° C. to 10° C. per minute and or 0.5° C. to 5° C. per minute. Different heating rates may be employed depending on the temperature range. Depending on the nature of the calcining atmosphere, the materials may be heated to the indicated temperatures for periods of time ranging from 1 to 60 hours or more, to produce a catalytically active product.

As used herein, the term "OSDA-depleted" (or composition having depleted OSDA) refers to a composition having a lesser content of OSDA after the treatment than before. In preferred embodiments, substantially all (e.g., greater than 90, 95, 98, 99, or 99.5 wt %) or all of the OSDA is removed by the treatment; in some embodiments, this can be confirmed by the absence of a TGA endotherm associated with the removal of the OSDA when the product material is subject to TGA analysis or the absence or substantial absence of C or N in elemental analysis (prior to heating, composition is expected to comprise C, N, O, Si, Al, H, and optionally Li, Na, K).

Further processing of these materials, whether modified or not, may also comprise contacting the isolated crystalline microporous aluminosilicate solid with ozone or other oxidizing agent at a temperature in a range of 100° C. to 200° C. for a time sufficient to form an OSDA-depleted aluminosilicate product. In certain of these embodiments, the heating is done at a temperature of about 150° C. to form an OSDA-depleted product. The ozone-treatment can be carried out in a flow of ozone-containing oxygen (typically for 12 hours or more. but shorter could be feasible). Any oxidative environment treatment sufficient to remove the OSDA can be used. Such environments, for example, can involve the use of organic oxidizers (alkyl or aryl peroxides or peracids) or inorganic peroxides (e.g., $H_2O_2$).

Further processing of these materials, whether modified or not, may also comprise, heating the isolated crystalline microporous aluminosilicate solid at a temperature in a range of from about 200° C. to about 600° C. in the presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In other aspects, the heating is done in the absence of these added salts. In certain of these embodiments, the heating is done in the presence of NaCl or KCl. In certain exemplary embodiments, the heating is done at a temperature in a range of from 500 to 600° C. In exemplary embodiments, the heating is done in either an oxidizing or inert atmosphere. In exemplary embodiments, the heating is done at a slow heating rate initially, e.g., from 0.1° C. to 10° C. per minute and/or from 0.5° C. to 5° C. per minute.

Such use of salts is consistent with the disclosures provided in US Patent Appl. Publ. No. 2002/0119887 to Q. Huo and N. A. Stephenson. For water removal, the aluminosilicate of GME topology is typically heated to 350° C. For substantial OSDA removal, temperatures up to 500° C. are typically employed. As described in Huo, the preferred salts include alkali metal (Li, Na, K, Rb, Cs) halides (preferably Cl); alkaline earth (Be, Mg, Ca, Sr, Be) nitrates or phosphates; aluminum, gallium, and indium carbonates; zinc sulfate; Ag, Cd borate or silicate; Ru, Rh, Pd, Pt, Au, or Hg carboxylates; La, Ce, Pr, Nd, Pm, or Sm sulfonates; Eu, Gd alkoxide; $R_{4-n}N^+H_n$ phenolates, where R is alkyl, n=0-4—as described in Huo. In some cases, the excess salt or salts can be removed, following calcination, by water (or other solvent) rinse or in a combination with ion-exchange and subsequent desolvation.

Once dehydrated or calcined, the dehydrated or OSDA-depleted crystalline microporous material may be treated with an aqueous ammonium or metal salt or may be treated under conditions so as to incorporate at least one type of alkaline earth metal or alkaline earth metal oxide or salt, or transition metal or transition metal oxide. In some embodiments, the salt is a halide salt. Where the salt is an ammonium salt, the resulting aluminosilicate contains the ammonium cation which, after calcination, decomposes to provide the protonated aluminosilicate (in the hydrogen form). In other embodiments, the metal salt comprises one or more of $K^+$, $Li^+$, $Na^+$, $Rb^+$, $Cs^+$:$Co^{2+}$, $Ca^{2+}$, $Mg^{2+}$, $Sr^{2+}$; $Ba^{2+}$; $Ni^{2+}$; or $Fe^{2+}$. In other specific embodiments, the metal cation salt is a copper salt, for example, Schweizer's reagent (tetraaminediaquacopper dihydroxide, $[Cu(NH_3)_4(H_2O)_2](OH)_2$), copper(II) nitrate, copper (II) diacetate (or other dicarboxylate), or copper(II) carbonate.

The addition of a transition metal or transition metal oxide may be accomplished, for example by chemical vapor deposition or chemical precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. This definition of transition metals also encompasses Group 4 to Group 12 elements. In certain independent embodiments, the transition metal or transition metal oxide comprises an element of Groups 6, 7, 8, 9, 10, 11, or 12. In other independent embodiments, the transition metal or transition metal oxide comprises scandium, yttrium, titanium, tin, zirconium, vanadium, manganese, chromium, molybdenum, tungsten, iron, ruthenium, osmium, cobalt, rhodium, iridium, nickel, palladium, platinum, copper, silver, gold, or mixtures. Fe, Ru, OS, Co, Rh, Ir, Ni, Pd, Pt, Cu, Ag, Au, and mixtures thereof are preferred.

Intermediate Reaction Compositions

As described herein, the as-formed and post-treated crystalline aluminosilicate compositions themselves are within the scope of the present disclosure and are considered to be independent embodiments of the present invention. All of the descriptions used to describe the features of the inventive processes are also considered to apply to these compositions. In an abundance of caution, some of these are presented here, but these descriptions should not be considered to exclude embodiments provided elsewhere.

Included in these embodiments are compositions comprising the aqueous compositions used in the hydrothermal treatments together with the respective crystalline microporous aluminosilicate products, wherein the aluminosilicate products contain the respective OSDAs used in their preparation occluded in their pores.

For example, in some embodiments, the composition comprises:

(a) a source of a silicon oxide, and optionally a source of germanium oxide, or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a mineralizing agent;

(d) an organic structure directing agent (OSDA) comprising at least one isomer of the quaternary piperidinium cation of Formula (I) (or any of the embodied cations of Formula (I) described elsewhere in this disclosure);
and (e) a compositionally consistent crystalline microporous aluminosilicate solid of GME topology.

As used herein, the term "compositionally consistent" refers to a crystalline aluminosilicate composition having a stoichiometry resulting from the crystallization of the of sources of oxides in the presence of piperidinium OSDAs; i.e., the OSDAs of Formula (I). In some of these embodiments, for example, this term reflects a composition which is the result of at least a partial progression of the hydrothermal treating process used to prepare these materials. Typically, these compositionally consistent crystalline microporous aluminosilicate solids contain, occluded in their pores, the OSDA used to make them; i.e., the OSDA present in the associated aqueous composition, and such is within the scope of the present disclosure.

In separate embodiments, these compositionally consistent crystalline microporous aluminosilicate solids may be substantially free of the OSDAs used in the aqueous media; in such embodiments, the aluminosilicate may be used as seed material for the crystallization.

These compositions may comprise any of the types and ratios of ingredients and may exist at temperatures consistent with the processing conditions described above as useful for the hydrothermal processing. It should be appreciated that this disclosure captures each and every of these permutations as separate embodiments, as if they were separately listed. In some embodiments, these compositions exist in the form of a gel or suspension.

Crystalline Microporous Compositions

In addition to the processing and process compositions, the microcrystalline products are also considered within the scope of the present invention. In particular, any product prepared by these inventive methods is considered an embodiment of this invention. Again, in preferred embodiments, the crystalline microporous aluminosilicate solid is preferably one of entirely GME topology. But separate embodiments also provide that the crystalline microporous solid may also contain other structural phases or phase mixtures, next to the GME phase.

These isolated microporous aluminosilicate solid of GME topology may contain any of the piperidinium OSDAs described herein occluded in their pores—i.e., the OSDAs of Formula (I) within the framework—or they may be devoid or substantially devoid of such organic materials (the terms "devoid" and "substantially devoid" being quantitatively analogous to the term "OSDA depleted").

The presence of the OSDAs may be identified using, for example $^{13}$C NMR, elemental analysis for C and N, or any of the methods defined in the Examples. It is a particular feature of the present invention that the cationic OSDAs retain their original structures, including their stereochemical conformations during the synthetic processes, these structures being compromised during the subsequent calcinations.

More specifically, some embodiments provide crystalline microporous aluminosilicate solids having pores at least some of which are occluded with quaternary piperidinium cations of Formula (I), in any of the embodiments described herein for these cations. In other embodiments, the pores are substantially OSDA-depleted.

Such aluminosilicate solids may also be described in terms of their Si:Al molar ratios, as well as their physical characteristics. In certain embodiments, the crystalline microporous aluminosilicate solid are characterized as having a molar ratio of Si:Al in a range of from 2.5 to about 100 (or $SiO_2/Al_2O_3$ ratio greater than 7 to about 30). Independent aspects of this embodiment include those where the Si/Al ratio is in a range of from 2.5 to 2.6, from 2.6 to 2.7, from 2.7 to 2.8, from 2.8 to 2.9, from 2.9 to 3, from 3 to 3.2, from 3.2 to 3.4, from 3.4 to 3.6, from 3.6 to 3.8, from 3.8 to 4, from 4 to 4.2, from 4.2 to 4.4, from 4.4 to 4.6, from 4.6 to 4.8, from 4.8 to 5, from 5 to 5.2, from 5.2 to 5.4, from 5.4 to 5.6, from 5.6 to 5.8, from 5.8 to 6 from 6 to 6.4, from 6.4 to 6.8, from 6.8 to 7.2, from 7.2 to 7.6, from 7.6 to 8, from 8 to 8.4, from 8.4 to 8.8, from 8.8 to 9.2, from 9.2 to 9.6 from 9.6 to 10, from 10 to 10.4, from 10.4 to 10.8, from 10.8 to 11.2, from 11.2 to 11.6, from 11.6 to 12, from 12 to 12.4, from 12.4 to 12.8, from 12.8 to 13.2, from 13.2 to 13.6, from 13.6 to 14.0, from 14 to 14.5, from 14.5 to 15, from 15 to 20, from 20 to 25, from 25 to 30, from 30 to 35, from 35 to 40, from 40 to 50, from 50 to 60, from 60 to 70, from 70 to 80, from 80 to 90, from 90 to 100, or any combination of two or more of these range, for example from 2.5 to 30, from greater than 3.5 (e.g., 3.6) to 100, or from greater than 3.5 to 30. In some embodiments where the aluminosilicate compositions contain occluded quaternary piperidinium OSDAs, the molar ratio of Si:Al is in any range or subrange of from 2.5 to about 100 described above. In other embodiments, where the aluminosilicate compositions contains no, or substantially no (e.g., substantially free of) quaternary piperidinium cation OSDA, the molar ratio of Si:Al is in any range or subrange of from greater than 3.5 to 100 described above.

The crystalline microporous aluminosilicate solids may also characterized by their physical properties. In specific embodiments, the crystalline microporous solid exhibits one or more of the characteristics associated with CIT-9. In other embodiments, these aluminosilicate solid exhibit at least one of the following characteristics:

(a) an XRD pattern having at least the five major peaks substantially as provided in Table 2.

Figure 10:
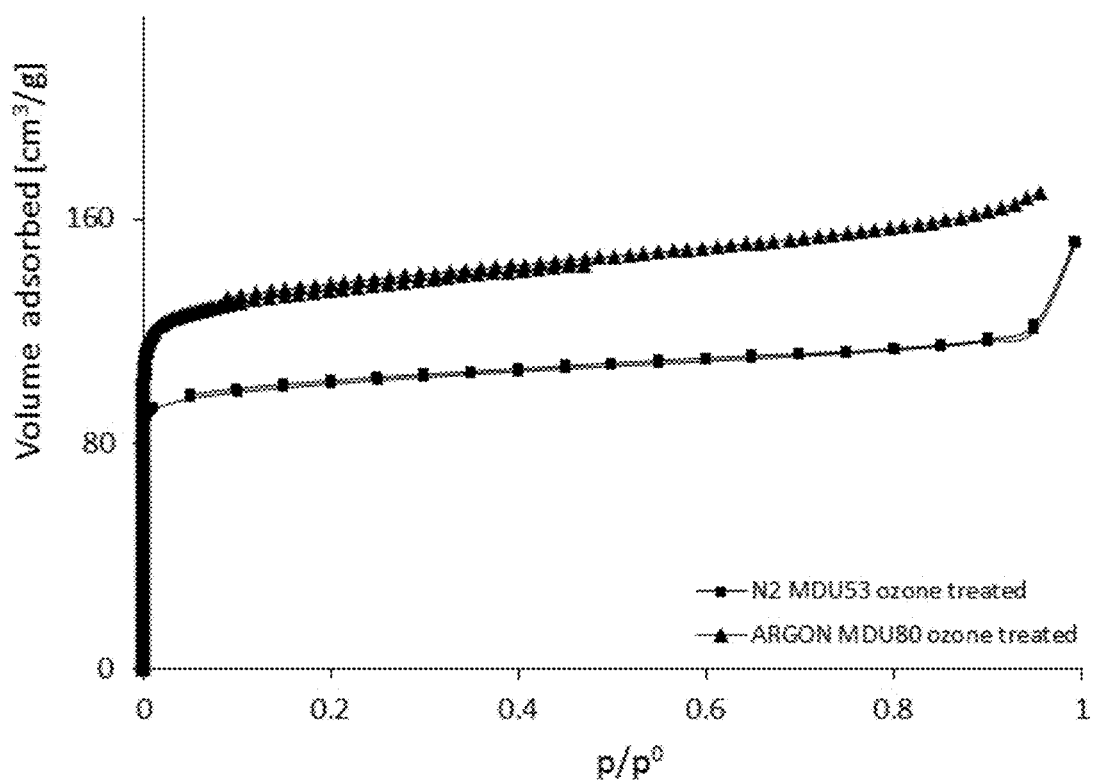
FIG. 10 shows a physisorption isotherm for MDU53 with N$_2$-gas and MDU80 with Argon after treatment with ozone at 150° C. for removal of the SDA.
Figure 11:
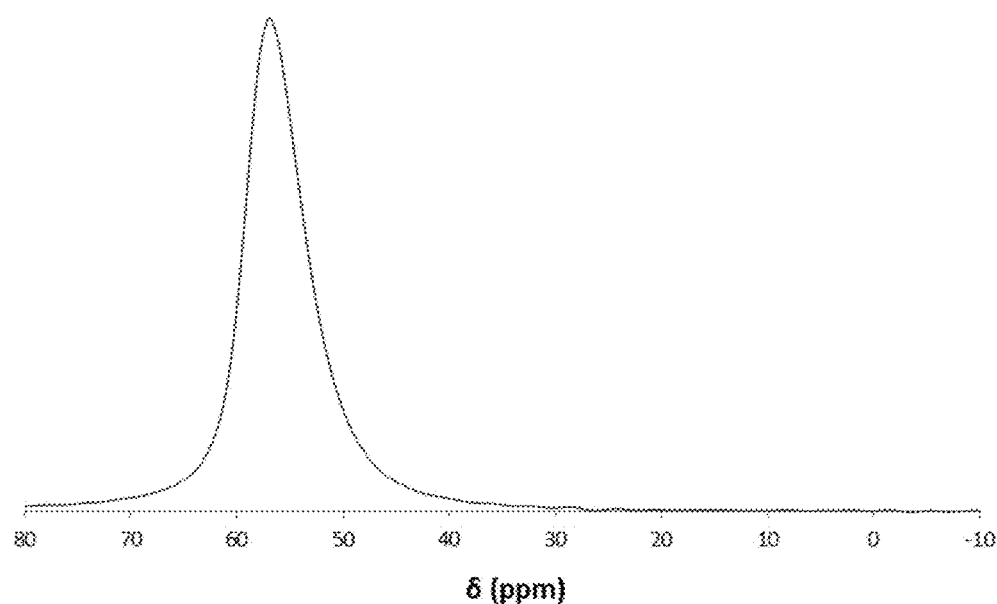
FIG. 11 shows an $^{27}$Al MAS NMR spectrum for MDU93 after ozone treatment, K-exchange and calcination. (300 MHz)
Figure 12:
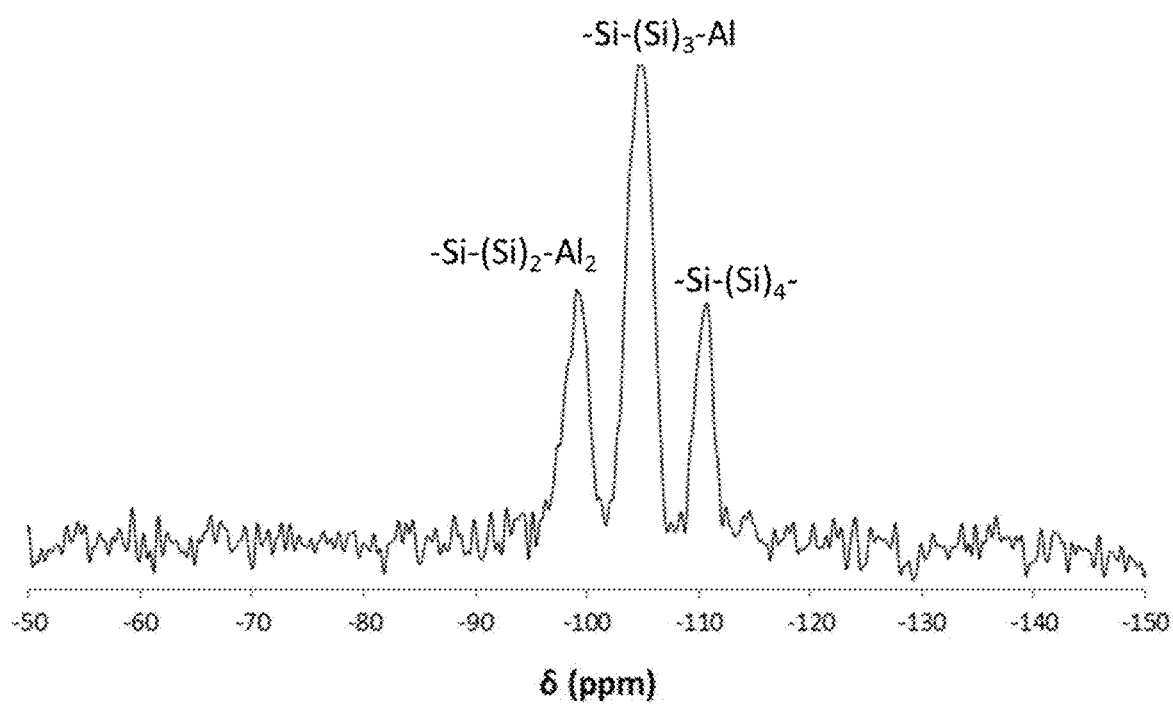
FIG. 12 shows $^{29}$Si MAS (Bloch Decay) NMR spectra for MDU93 after ozone-treatment, K-exchange and calcination. (500 MHz).

(b) an XRD diffraction pattern the same as or consistent with any one of those shown in FIG. 3, FIG. 6, FIG. 7, or FIG. 13;

(c) an $^{29}$Si MAS spectrum having a plurality of chemical shifts of about −99.1, −104.9 and −110.5 ppm downfield of a peak corresponding to and external standard of tetramethylsilane;

(d) an $^{29}$Si MAS spectrum the same as or consistent with the one shown in FIG. 12;

(f) an physisorption isotherm with $N_2$-gas or with argon the same as or consistent with any one of those shown in FIG. 10; or (e) an $^{27}$Al MAS NMR spectrum the same as or consistent with the one shown in FIG. 11.

Figure 4:
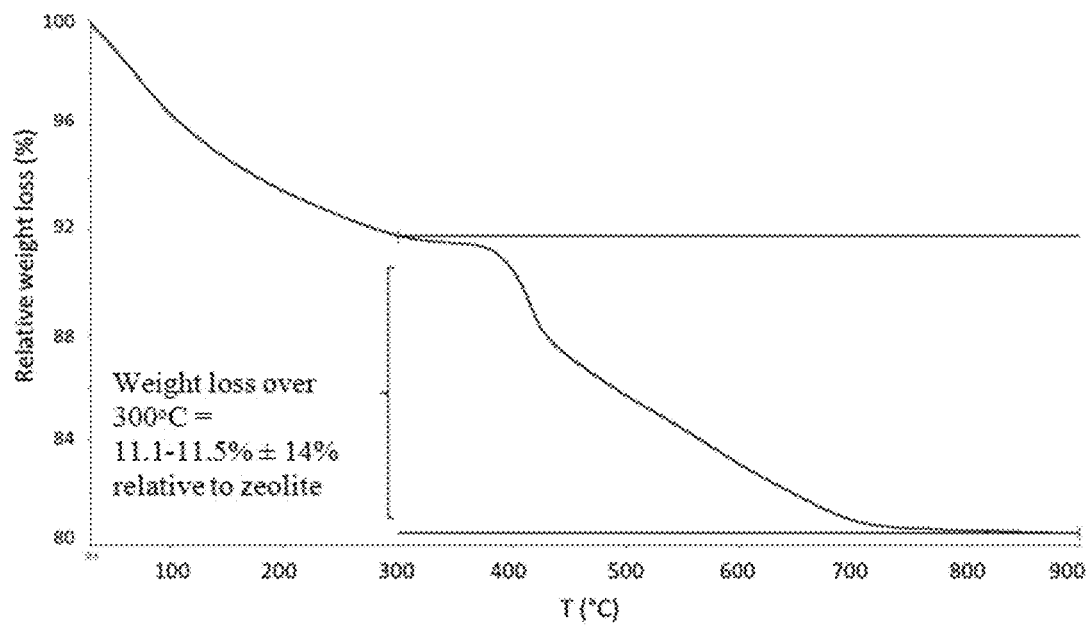
FIG. 4 shows thermogravimetric analysis curves derived from an as-made CIT-9 from Table 1, entry 1: MDU80

Additional embodiments include those compositions which exhibit (f) a thermogravimetric analysis curve the same as or consistent with the one shown in FIG. 4; the TGA indicative of a loss of 8 to 16 wt %, possibly due to the removal of the OSDA; (g) a $^{13}$C CP MAS NMR spectra the same as or consistent with the one shown in FIG. 5.

The disclosed crystalline microporous aluminosilicate compositions include those which result from the post-treatment or further processing described in the processing section. These include those aluminosilicates which are in their hydrogen forms or have cations, metals or metal oxides within their pore structures. Accordingly, in certain embodiments, the microporous aluminosilicate solids have GME topologies, containing Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4 in at least some of their pores. In specific aspects of these embodiments, these pores contain NaCl or KCl.

Additional embodiments include those crystalline microporous aluminosilicate solids having GME topology, at least some of whose pores transition metals, transition metal oxides, or salts, for example scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one specific embodiment, the pores of the aluminosilicate solids contain copper, as metal, oxide, or salt.

Use of the Inventive Compositions

The calcined crystalline microporous solids, calcined or doped or treated with the catalysts described herein may also be used as catalysts for a variety of chemical reactions, including carbonylating DME with CO at low temperatures, reducing NOx with methane, reducing NOx with ammonia, cracking, dehydrogenating, converting paraffins to aromatics, MTO (methanol-to-olefin), isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with a catalyst comprising one or more of the crystalline microporous aluminosilicate solids described herein under conditions sufficient to affect the named transformation. These catalysts appear to be especially suitable for converting paraffins into aromatics (e.g., hexane to benzene) and for carbonylating DME with CO at low temperatures.

The GME framework topology is also interesting for applications in sorption. Sorption applications could potentially be found in hydrocarbon separation processes and ion-exchange. Catalytic processes of interest include, but are not limited to, the aromatization of naphtha, the dehydrocyclization of hexane, hydrocarbon isomerization and/or chlorination.

Specific conditions for many of these transformations are known to those of ordinary skill in the art. Exemplary conditions for such reactions/transformations may also be found in WO/1999/008961 and U.S. Pat. No. 4,544,538, both of which are incorporated by reference herein in its entirety for all purposes.

Depending upon the type of reaction that is catalyzed, the microporous solid may be predominantly in the hydrogen form, partially acidic or substantially free of acidity. As used herein, "predominantly in the hydrogen form" means that, after calcination (which may also include exchange of the pre-calcined material with $NH_4^+$ prior to calcination), at least 80% of the cation sites are occupied by hydrogen ions and/or rare earth ions.

The following listing of embodiments is intended to complement, rather than displace or supersede, any of the previous descriptions.

Embodiment 1. A process for preparing an aluminosilicate composition having a GME topology, the process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a mineralizing agent; and (d) an organic structure directing agent (OSDA) comprising at least one isomer of the quaternary piperidinium cation of Formula (I):

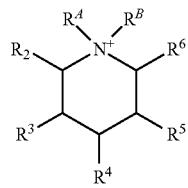

(I)

under conditions effective to crystallize a crystalline microporous aluminosilicate solid of GME topology; wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiments, the crystalline microporous aluminosilicate solid of GME topology has a molar ratio of Si:Al greater than 3.5.

In some Aspects of this Embodiment, the OSDA comprises at least one isomer of the quaternary piperidinium cation of Formula (IA) or (IB):

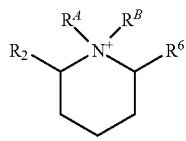

(IA)

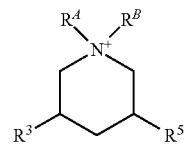

(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion.

Embodiment 2. The process of Embodiment 1, wherein the quaternary piperidinium cation of Formula (I) is or comprises an N,N-dialkyl-2,6-lupetidinium cation or an N,N-dialkyl-3,5-lupetidinium cation:

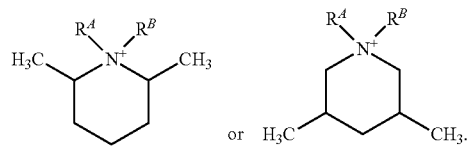

In separate Aspects of this Embodiment, the quaternary piperidinium cation of Formula (I) is an N,N-dialkyl-2,6-lupetidinium cation. In other Aspects, it is an N,N-dialkyl-3,5-lupetidinium cation.

Embodiment 3. The process of Embodiment 1 or 2, wherein the quaternary piperidinium cation of Formula (I) is or comprises cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

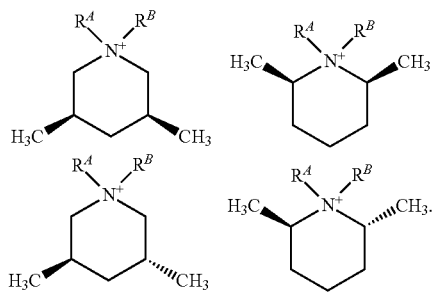

Each of these cations is an independent Aspect of this Embodiment.

Embodiment 4. The process of Embodiment 2 or 3, wherein $R^{A'}$ and $R^B$ are both methyl.

Embodiment 5. The process of any one of Embodiments 1 to 4, wherein the quaternary piperidinium cation has an associated fluoride or hydroxide ion preferably substantially free of other halide counterions. In separate Aspects of this Embodiment, the associated anion is hydroxide.

Embodiment 6. The process of any one of Embodiments 1 to 5, wherein the composition being hydrothermally treated is or comprises a source of silicon oxide and a source of aluminum oxide. In other Aspects of this Embodiment, some of the sources of silicon oxide and aluminum oxide derive from common sources, for example, an aluminosilicate. In other Aspects of this Embodiment, the composition is absent any source of one or more of boron oxide, gallium oxide, germanium oxide, hafnium oxide, iron oxide, tin oxide, titanium oxide, indium oxide, vanadium oxide, or zirconium oxide.

Embodiment 7. The process of any one of Embodiments 1 to 6, wherein the source of aluminum oxide, silicon oxide, or optional source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, mixed metal oxide, or combination thereof.

Embodiment 8. The process of any one of Embodiments 1 to 7, wherein the source of silicon oxide is or comprises an aluminosilicate, a silicate, silica hydrogel, silicic acid, fumed silica, colloidal silica, tetra-alkyl orthosilicate, a silica hydroxide or combination thereof. It should be appreciated that in certain Aspects of this Embodiment, the aluminosilicate or silicate is of a topology or composition different than the topology or composition of the intended product (e.g., different than the GME topology eventually prepared and/or isolated). In other Aspects of this Embodiment, the aluminosilicate or silicate is the same topology or composition as the topology or composition of the intended product, for example, acting as seeds.

Embodiment 9. The process of any one of Embodiments 1 to 8, wherein the source of aluminum oxide is or comprises an alkoxide, hydroxide, or oxide of aluminum, a sodium aluminate, an aluminum siloxide, an aluminosilicate, or combination thereof. It should be appreciated that in certain Aspects of this Embodiment, the aluminosilicate is of a topology or composition different than the topology or composition of the intended product (e.g., different than the GME topology eventually prepared and/or isolated). In other Aspects of this Embodiment, the aluminosilicate is the same topology or composition as the topology or composition of the intended product, for example, acting as seeds Embodiment 10. The process of any one of Embodiments 1 to 9, wherein the source of silicon oxide is or comprises sodium silicate, for example from a FAU-zeolite. In certain Aspects of this Embodiment, the FAU-zeolite may also provide at least a part of the source of aluminum oxide.

Embodiment 11. The process of any one of Embodiments 1 to 10, wherein the mineralizing agent is or comprises an aqueous hydroxide. In certain Aspects of this Embodiment, the hydroxide is an alkali metal or alkaline earth metal hydroxide, for example including LiOH, NaOH, KOH, RbOH, CsOH, $Mg(OH)_2$, $Ca(OH)_2$, $Sr(OH)_2$, or $Ba(OH)_2$.

Embodiment 12. The process of any one of Embodiments 1 to 11, wherein the molar ratio of Al:Si is in a range of from 0.0067 to 0.5 (or the molar ratio of Si:Al is in a range of from 2 to 150). In certain specific Aspects of this Embodiment, the molar ratio of Al:Si is in a range of from 0.01 to 0.5, or from 0.05 to 0.15.

Embodiment 13. The process of any one of Embodiments 1 to 12, wherein the molar ratio of OSDA:Si is in a range of from 0.01 to 0.75. In certain specific Aspects of this Embodiment, the molar ratio of OSDA:Si is in a range of from 0.01 to 0.5, or from 0.1 to 0.5.

Embodiment 14. The process of any one of Embodiments 1 to 13, wherein the molar ratio of water:Si is in a range of from 5 to 50. In certain specific Aspects of this Embodiment, the molar ratio of water:Si is in a range of from 10 to 50 or from 10 to 25.

Embodiment 15. The process of any one of Embodiments 1 to 14, wherein the molar ratio of total hydroxide:Si is in a range of 0.1 to 1.25. In certain specific Aspects of this Embodiment, the molar ratio of total hydroxide:Si is in a range of from 0.5 to 1.

Embodiment 16. The process of any one of Embodiments 1 to 15, wherein the conditions effective to crystallize a crystalline microporous solid of GME topology include treatment of the hydrothermally treated composition at a temperature in a range of from 100° C. to 200° C. In certain specific Aspects of this Embodiment, the temperature is in a range of from 120° C. to 180° C. In certain independent Aspects of this Embodiment, the times and temperatures include ranges described elsewhere herein.

Embodiment 17. The process of any one of Embodiments 1 to 14, wherein the hydrothermally treating is done at a temperature in a range of from about 100° C. to about 200° C. for a time effective for crystallizing the crystalline microporous solid of GME topology. In certain specific Aspects of this Embodiment, this time is in a range of from 1 hour to 14 days. In certain independent Aspects of this Embodiment, the times and temperatures include ranges described elsewhere herein.

Embodiment 18. The process of any one of Embodiments 1 to 17, further comprising isolating the crystalline microporous aluminosilicate solid of GME topology.

Embodiment 19. The process of Embodiment 18, further comprising heating the isolated crystalline microporous solid at a temperature in a range of from about 250° C. to about 450° C. to form an OSDA-depleted product. In certain independent Aspects of this Embodiment, the heating is done in an oxidizing atmosphere, such as air or oxygen, or in the presence of other oxidizing agents. In other Aspects, the heating is done in an inert atmosphere, such as argon or nitrogen.

Embodiment 20. The process of Embodiment 18, further comprising contacting the isolated crystalline microporous solid with ozone or other oxidizing agent at a temperature in a range of 100° C. to 200° C. for a time sufficient to form an OSDA-depleted crystalline microporous solid. In certain specific Aspects of this Embodiment, the heating is done at a temperature of about 150° C. to form an OSDA-depleted product. In other Aspects of this Embodiment, the heating is done for a time sufficient to substantially remove any occluded OSDA from the pores of the zeolite.

Embodiment 21. The process of Embodiment 18, further comprising heating the isolated crystalline microporous solid at a temperature in a range of from about 200° C. to about 600° C. in the absence or presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In certain Aspects of this Embodiment, the heating is done in the presence of NaCl or KCl. Aspects of this Embodiment, the heating is done at a temperature in a range of from 500 to 600° C. In still other Aspects of the Embodiment, the heating is done in either an oxidizing or inert atmosphere.

Embodiment 22. The process of any one of Embodiments 19 to 21, further comprising treating the dehydrated or OSDA-depleted product with an aqueous alkali, alkaline earth, transition metal, rare earth metal, ammonium or alkylammonium salts, preferably a halide salt. In some Aspects of this Embodiment, the salt is a halide salt. In some Aspects of this Embodiment, the metal salt comprises $K^+$, $Li^+$, $Rb^+$, $Cs^+$:$Co^{2+}$, $Ca^{2+}$, $Mg^{2+}$, $Sr^{2+}$; $Ba^{2+}$; $Ni^{2+}$; $Fe^{2+}$. In other specific Aspects, the metal cation salt is a copper salt, for example, Schweizer's reagent (tetraamminediaquacopper dihydroxide, [Cu(NH$_3$)$_4$(H$_2$O)$_2$](OH)$_2$]), copper(II) nitrate, or copper(II) carbonate.

Embodiment 23. The process of any one of Embodiments 19 to 22, further comprising treating at least some pores of the calcined crystalline microporous solid with at least one type of transition metal or transition metal oxide. In certain Aspects of this Embodiment, the transition metal or transition metal oxide comprises a Group 4 to Group 12 metal. In certain independent Aspects of this Embodiment, the transition metal or transition metal oxide comprises an element of Groups 6, 7, 8, 9, 10, 11, or 12. In other independent Aspects of this Embodiment, the transition metal or transition metal oxide comprises Fe, Ru, OS, Co, Rh, Ir, Ni, Pd, Pt, Cu, Ag, or Au.

Embodiment 24. A composition prepared by any one of the processes of Embodiments 1 to 23. In certain Aspects of this Embodiment, the composition comprises an aluminosilicate having a molar ratio of Si:Al is in a range of from about 2.5 to 100. Independent Aspects of this Embodiment include those described elsewhere herein in this context.

Embodiment 25. A composition comprising:
(a) a source of a silicon oxide, and optionally a source of germanium oxide, or combination thereof;
(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof;
(c) a mineralizing agent (preferably hydroxide);
(d) an organic structure directing agent (OSDA) comprising at least one isomer of the quaternary piperidinium cation of Formula (I):

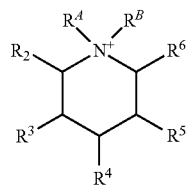

(I)

and
(e) a compositionally consistent crystalline microporous aluminosilicate solid of GME topology;
wherein
$R^A$ and $R^B$ are independently a $C_{1-3}$ alkyl, or together with the N to which they are bound form a 5 or 6 membered saturated or unsaturated ring; and
$R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiments, the crystalline microporous aluminosilicate solid of GME topology has a molar ratio of Si:Al in a range of from 2.5 to 100, or any of the subranges described in this context, elsewhere herein.

In other Aspects of this Embodiment, the OSDA comprises at least one isomer of the quaternary piperidinium cation of Formula (I):

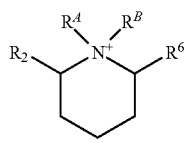

(IA)

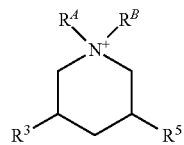

(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion. Each of these cations is an independent Aspect of this Embodiment. In certain Aspects of this Embodiment, the composition is one characterized as a CIT-9 composition as described herein. In other Aspects of this Embodiment, the composition is absent any source of aluminum oxide, boron oxide, gallium oxide, hafnium oxide, iron oxide, tin oxide, titanium oxide, indium oxide, vanadium oxide, or zirconium oxide.

Embodiment 26. The composition of Embodiment 25, wherein the quaternary piperidinium cation of Formula (I) is an N,N-dialkyl-2,6-lupetidinium cation or N,N-dialkyl-3,5-lupetidinium cation:

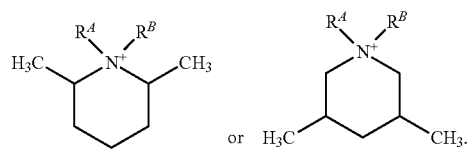

Embodiment 27. The composition of Embodiment 25, wherein the quaternary piperidinium cation of Formula (I) is cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof or a mixture of OSDAs containing these cations:

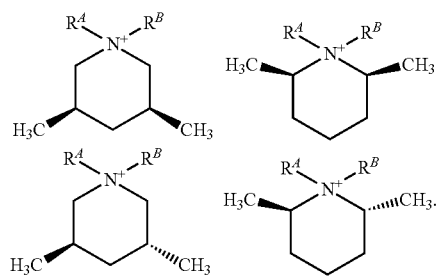

Each of these cations is an independent Aspect of this Embodiment.

Embodiment 28. The composition of Embodiment 26 or 27, wherein $R^{A'}$ and $R^B$ are both methyl.

Embodiment 29. The composition of any one of Embodiments 25 to 28, containing a source of silicon oxide and a source of aluminum. In certain Aspects of this Embodiment, the optionally sources of germanium oxide, boron oxide, gallium oxide, hafnium oxide, iron oxide, tin oxide, titanium oxide, indium oxide, vanadium oxide, or zirconium oxide are absent.

Embodiment 30. The composition of any one of Embodiments 25 to 29, wherein the source of silicon oxide is or comprises an aluminosilicate, a silicate, silica hydrogel, silicic acid, fumed silica, colloidal silica, tetra-alkyl orthosilicate, a silica hydroxide or combination thereof.

Embodiment 31. The composition of any one of Embodiments 25 to 30, wherein the source of aluminum oxide is or comprises an alkoxide, hydroxide, or oxide of aluminum, a sodium aluminate, an aluminum siloxane, an aluminosilicate, or combination thereof.

Embodiment 32. The composition of any one of Embodiments 25 to 31, wherein the source of silicon oxide is or comprises sodium silicate and the source of Al is or comprises a FAU-zeolite Embodiment 33. The composition of any one of Embodiments 25 to 32, wherein the mineralizing agent comprises aqueous hydroxide. In certain Aspects of this Embodiment, the hydroxides is an alkali metal or alkaline earth metal hydroxide, including LiOH, NaOH, KOH, RbOH, CsOH, $Mg(OH)_2$, $Ca(OH)_2$, $Sr(OH)_2$, or $Ba(OH)_2$.

Embodiment 34. The composition of any one of Embodiments 25 to 33, wherein the molar ratio of Al:Si in the composition is in a range of 0.0067 to 0.5 (or the molar ratio of Si:Al is in a range of from 2 to 150). In certain specific Aspects of this Embodiment, the molar ratio of Al:Si is in a range of from 0.01 to 0.5, or from 0.05 to 0.15.

Embodiment 35. The composition of any one of Embodiments 25 to 34, wherein the molar ratio of OSDA:Si in the composition is in a range of from 0.01 to 0.75. In certain specific Aspects of this Embodiment, the molar ratio of OSDA:Si is in a range of from 0.01 to 0.5, or from 0.1 to 0.5

Embodiment 36. The composition of any one of Embodiments 25 to 35, wherein the molar ratio of water:Si in the composition is in a range of from 5 to 75. In certain specific Aspects of this Embodiment, the molar ratio of water:Si is in a range of from 10 to 50 or from 10 to 25.

Embodiment 37. The composition of any one of Embodiments 25 to 36, wherein the molar ratio of total hydroxide:Si in the composition is in a range of 0.1 to 1.25. In certain specific Aspects of this Embodiment, the molar ratio of total hydroxide:Si is in a range of from 0.5 to 1.

Embodiment 38. The composition of any one of Embodiments 25 to 37 that is a suspension or gel.

Embodiment 39. A crystalline microporous aluminosilicate solid of GME topology having pores at least some of which are occluded with at least one isomer of the quaternary piperidinium cation of Formula (I):

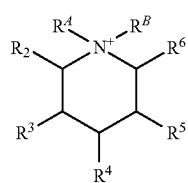

(I)

wherein
$R^A$ and $R^B$ are independently a $C_{1-3}$ alkyl, or together with the N to which they are bound form a 5 or 6 membered saturated or unsaturated ring; and
$R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiments, the crystalline microporous aluminosilicate solid of GME topology has a molar ratio of Si:Al greater than 3.5.

In other Aspects of this Embodiment, the OSDA is or comprises at least one isomer of the quaternary piperidinium cation of Formula (IA) or (IB):

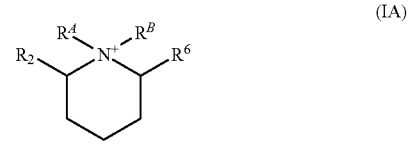

(IA)

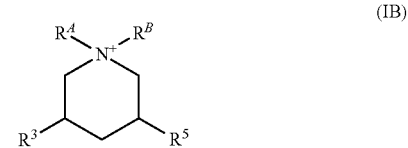

(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion. In certain Aspects of this Embodiment, the composition is one characterized as a CIT-9 composition as described herein.

Embodiment 39. The crystalline microporous solid of Embodiment 35 or 36, wherein the quaternary piperidinium cation of Formula (I) or (II) is an N,N-dialkyl-2,6-lupetidinium cation or N,N-dialkyl-3,5-lupetidinium cation:

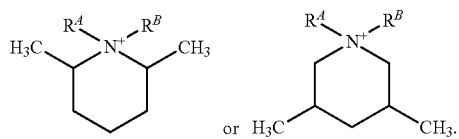

Each of these cations is an independent Aspect of this Embodiment.

Embodiment 40. The crystalline microporous solid of any one of Embodiments 35 to 37, wherein the quaternary piperidinium cation of wherein the quaternary piperidinium cation of Formula (I) or (II) is cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof or a mixture of OSDAs containing such a cation:

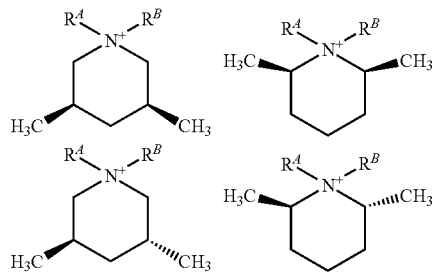

Each of these cations is an independent Aspect of this Embodiment.

Embodiment 41. The crystalline microporous solid of any one of Embodiments 39 to 41, wherein $R^{A^t}$ and $R^B$ are both methyl.

In certain Aspects, the crystalline microporous aluminosilicate of any one of Embodiments 39 to 41 has a Si/Al molar ratio in a range of from 2.5 to about 100 (or $SiO_2/Al_2O_3$ ratio greater than 5 to about 200). Independent Aspects of this Embodiment include those described elsewhere herein in this context. In specific Aspects of this Embodiment, the crystalline microporous solid exhibits one or more of the characteristics associated with CIT-9.

Embodiment 42. A crystalline microporous solid comprising (a) silicon oxide, and optionally germanium oxide, or combination thereof and (b) aluminum oxide, and optionally boron oxide, gallium oxide, hafnium oxide, iron oxide, tin oxide, titanium oxide, indium oxide, vanadium oxide, zirconium oxide, or combination thereof, and having a GME topology and the solid exhibiting at least one of the following:

(a) an XRD pattern having at least the five major peaks substantially as provided in Table 2.

(b) an XRD diffraction pattern the same as or consistent with any one of those shown in FIG. 3, FIG. 6, FIG. 7, or FIG. 13;

(c) an $^{29}Si$ MAS spectrum having a plurality of chemical shifts of about −99.1, −104.9 and −110.5 ppm downfield of a peak corresponding to and external standard of tetramethylsilane;

(d) an $^{29}Si$ MAS spectrum the same as or consistent with the one shown in FIG. 12;

(f) an physisorption isotherm with $N_2$-gas or with argon the same as or consistent with any one of those shown in FIG. 10;

(e) an $^{27}Al$ MAS NMR spectrum the same as or consistent with the one shown in FIG. 11;

(f) a molar ratio of Si:Al that is greater than 3.5 to about 100 (or $SiO_2/Al_2O_3$ ratio greater than 7 to about 200); or (g) a molar ratio of Si:Al that is greater than 2.5 to about 100 (or $SiO_2/Al_2O_3$ ratio greater than 7 to about 200), wherein the crystalline microporous solid contains at least one quaternary piperidinium cation of Formula (I).

Additional Aspects of this Embodiment embodiments include those compositions which exhibit (f) a thermogravimetric analysis curve the same as or consistent with the one shown in FIG. 4; the TGA indicative of a loss of 8 to 16 wt %, possibly due to the removal of the OSDA; (g) a $^{13}C$ CP MAS NMR spectra the same as or consistent with the one shown in FIG. 5. In specific Aspects of this Embodiment, the crystalline microporous solid exhibits one or more of the characteristics associated with CIT-9.

Embodiment 43. A crystalline microporous aluminosilicate of GME topology having a Si/Al molar ratio in a range of from greater than 3.5 to about 100 (or $SiO_2/Al_2O_3$ ratio greater than 7 to about 200). Independent Aspects of this Embodiment include those where the molar Si/Al ratio is described elsewhere herein. In certain Aspects of this Embodiment, the crystalline microporous aluminosilicate contains one or more of the quaternary piperidinium-containing OSDA described herein occluded within its pores. In other Aspects, the crystalline microporous aluminosilicate is devoid or substantially devoid of such piperidinium-containing OSDAs. Aspects of this Embodiment, the crystalline microporous solid exhibits one or more of the characteristics associated with CIT-9.

Embodiment 44. The crystalline microporous solid of Embodiment 42 or 43, comprising pores, at least some of which contain Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4. In specific Aspects of this Embodiment, the pores contain NaCl or KCl.

Embodiment 45. The crystalline microporous solid of any one of Embodiments 42 to 44, comprising pores, at least some of which contain scandium, yttrium, titanium, tin, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one Aspect of this Embodiment, the pores contain copper, as metal, oxide, or salt.

Embodiment 46. A process comprising carbonylating DME with CO at low temperatures, reducing NOx with methane, cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with a catalyst comprising the crystalline microporous solid of any one of Embodiments 42 to 45 under conditions sufficient to affect the named transformation. In specific Aspects of this Embodiments, the process comprises converting paraffins into aromatics (hexane to benzene) and carbonylating DME with CO at low temperatures

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric, or autogenous for the solution at that temperature.

Example 1. General Methods

Example 1.1. Materials and Methods

N,N-dimethyl-3,5-lupetidinium hydroxide was acquired from SACHEM Inc.

All PXRD characterization was conducted on a Rigaku MiniFlex II with Cu $K_\alpha$ radiation.

$^{13}C$ CP MAS solid state NMR MAS spectra were recorded on a Bruker 500 MHz spectrometer in a 4 mm $ZrO_2$ rotor spinning at 8 kHz and referenced to adamantane as external standard. Solid-state $^{27}Al$ MAS NMR was acquired on a Bruker AM 300 MHz spectrometer operated at 78.2 MHz using a 90° pulse length of 2 μs and a cycle delay time of 1 s. Samples were loaded in a 4 mm $ZrO_2$ rotor and spun at 12 kHz. Chemical shifts were referenced to 1 M aqueous aluminum nitrate solution. $^{29}Si$ NMR was measured on a Bruker 500 MHz spectrometer in a 4 mm $ZrO_2$ rotor at a spinning rate of 8 kHz and referenced externally versus tetramethylsilane.

Thermogravimetric analysis (TGA) was performed on a Perkin Elmer STA 6000 with a ramp of 10° C.min$^{-1}$ to 900° C. under air atmosphere.

SEM was performed on a ZEISS 1550 VP FESEM, equipped with an Oxford X-Max SDD X-ray Energy Dispersive Spectrometer (EDS) system for determining the Si/Al ratios of the samples.

The N$_2$ and Ar adsorption isotherms were performed at −196° C. and −186° C. respectively, with a Quantachrome Autosorb iQ instrument. Prior to analysis, the samples were outgassed under vacuum at 200° C. The t-plot method was used to calculate the micropore volumes on the adsorption branch.

Example 1.2. General Synthetic Methods

Syntheses in Table 1 were performed with this OSDA in its hydroxide form. A general procedure for hydroxide syntheses was as follows. The OSDA in its hydroxide form was combined with additional base (1M sodium hydroxide, RT Baker) and water in a 23 mL-Teflon Parr reactor. Then a silica source was added (N° Sodium silicate (PQ Corporation) as well as an aluminum source (CBV500=NH$_4$-FAU of Zeolyst). The synthesis was stirred until a homogenous gel was obtained. The Teflon Parr reactor was then sealed and placed in a rotating or static oven at 140° C. Aliquots of the synthesis gels were taken periodically as follows: quenching the reactor in water, opening the reactor, stirring its contents till homogeneous and finally, removing enough material for PXRD. After washing the aliquots once with water and once with acetone, they are left to dry in a 100° C. oven before PXRD measurement. The yields were calculated as follows: the final dry weight obtained after thorough washing of the finished syntheses with water and acetone and drying at 100° C. is corrected with the weight loss of organic OSDA and water in TGA up to 900° C. This corrected weight is assumed to be pure aluminosilicate and is divided by the maximum theoretical possible aluminosilicate formation from the input silica and alumina. The weight of sodium cation present in the samples is hereby neglected.

The ozonolysis procedure for SDA removal was carried out at 150° C. in a tube furnace by using a Longevity Resources ozone generator (setting at 2) and an oxygen gas flow of 200 cm$^3$/min over 100-500 mg of as-made zeolite sample. Ion-exchanges were performed in 1M nitrate salt solutions at 80° C. for 2 h under stirring with 1 g zeolite per 100 mL and this was repeated 3 times.

The calcination of K$^+$-CIT-9 was performed in dry flowing air by heating to 150° C. at 1° C./min; holding for 3 h at 150° C., and then heated further to 580° C. at 1° C./min and held for 6 h.

Example 2. Syntheses and Characterizations

Figure 2:
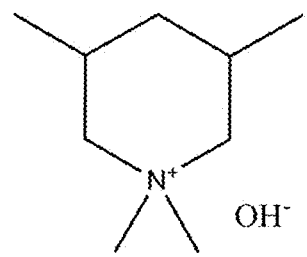
FIG. 2 shows a structure of quaternized N,N-dimethyl-3,5-dimethylpiperidine, one of the OSDAs of the instant disclosure.

Table 1 shows typical CIT-9 (GME) syntheses. It was found that pure GME could be made, free of powder X-ray diffraction (PXRD)-visible CHA impurities (usually seen at 2θ values of 9.4; 15.9 and 20.4), using the quaternized N,N-dimethyl-3,5-dimethylpiperidine structure directing agent. This OSDA is structurally illustrated in FIG. 2.

TABLE 1

Typical CIT-9 (GME) syntheses reactions with N,N-dimethyl-3,5-dimethylpiperidine hydroxide (98 cis/2% trans) as the OSDA, NH$_4$-FAU (CBV500, Si/Al 2.6) as aluminum source and sodium silicate as silicon source.

| | Gel composition relative to Si[1] (i.e., molar ratios based on Si = 1) | | | | | Time | | | TGA[2] | Yield | Sample |
|---|---|---|---|---|---|---|---|---|---|---|---|
| Entry | Al | OSDA | H$_2$O | OH$^-$ | NaOH | (h) | phase | Si/Al | (wt %) | (%) | name |
| 1 | 0.067 | 0.17 | 20.7 | 0.71 | 0.54 | 54 | GME | 4.0 | 14.1% | 24% | MDU80 |
| 2[3] | 0.067 | 0.17 | 19.9 | 0.71 | 0.54 | 48 | GME | 4.0 | 13.7% | 35% | MDU93 |
| 3 | 0.066 | 0.17 | 20.5 | 0.70 | 0.53 | 63 | GME[4] | 5.0 | 12.3% | 33%[5] | MDU53 |
| 4 | 0.022 | 0.17 | 20.1 | 0.76 | 0.59 | 54 | GME | 4.8 | — | <10%[6] | MDU22 |
| 5 | 0.033 | 0.17 | 20.0 | 0.74 | 0.57 | 54 | GME[7] | — | — | — | MDU19 |
| 6 | 0.033 | 0.14 | 11.9 | 0.71 | 0.57 | 48 | GME | 4.1 | 15.6% | 13% | MDU190 |
| 7[8] | 0.33 | 0.375 | 22.1 | 0.875 | 0.5 | 48 | GME[9] | n.d. | n.d. | n.d. | — |

[1]NaOH:Si is calculated from the total Na content, originating from NaOH addition and sodium silicate. Synthesis in rotating oven at 140° C. OH$^-$ is the sum of inorganic and OSDA derived hydroxide contents.
[2]Weight % loss in TGA between 300° C. and 900° C. relative to the amount of zeolite left at 900° C.
[3]Syntheses in a static oven at 140° C.
[4]ANA impurity (dense phase).
[5]Yield after 115 h, but both PXRD at 63 h and 115 h were absent of starting FAU. After 63 h, the ANA impurity reflections became more intense,
[6]Yield after 7 days, but PXRD after 54 h and 7 days were identical and absent of starting FAU.
[7]AEI impurity.
[8]Using 50/50 cis-trans N,N-dimethyl-3,5-dimethylpiperidine hydroxide.
[9]ANA impurity.

Figure 3:
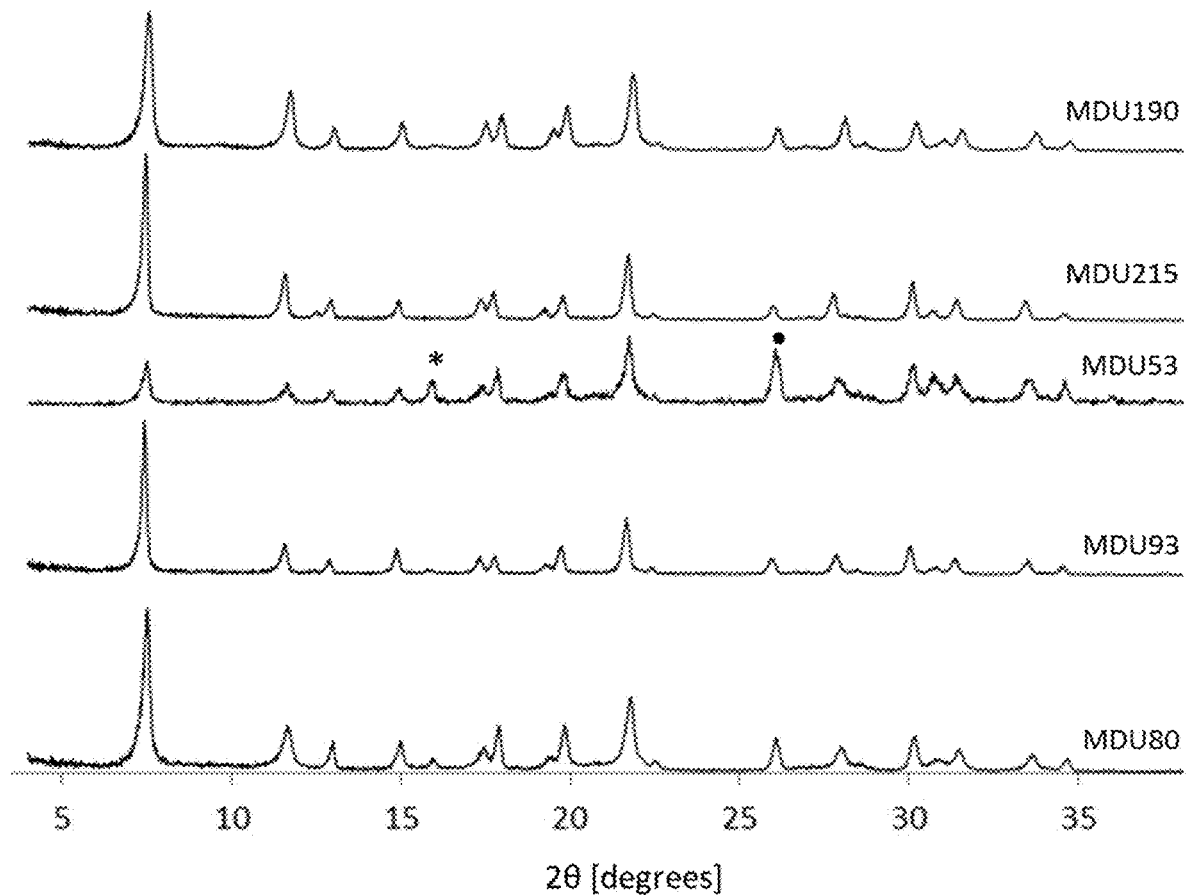
FIG. 3 shows PXRD traces of CIT-9 (GME) produced in different gels according to Table 1. *ANA impurity; ˙ANA impurity combined with a GME reflection.

Table 1 shows a range of successful GME syntheses conditions. Furthermore, it is seen in these examples that the molar Si/Al ratios of the obtained materials with the GME topology had a Si/Al ratio around 4 to 5 and always higher than 3.5. Other compositions having Si/Al ratios below or above the exemplified examples can also be prepared. The corresponding silica/alumina ratios were thus around 8 to 10 and always higher than 7 in these syntheses. To date, commonly reported GME aluminosilicates have a silica/alumina ratio below 5. The significant differences in composition from previously reported GME aluminosilicates provide the basis for naming this material as CIT-9. It is expected that simple modifications of the described methods will yield GME materials with even higher Si/Al ratios, as this is usually the case for OSDA-mediated synthesis. CIT-9 was made statically or in a rotating oven, as evidenced from Entry 1 and 2. CIT-9 was also made from gels with a Si/Al content of 15 up to 45 (e.g. Entry 3, 4 and 5) and also with other FAU. CIT-9 was also made in lower H$_2$O:Si gels (entry 6). FIG. 3 and Table 2 shows the PXRD diffraction pattern of some of the typical CIT-9 materials made in Table 1. All reflections match with the reported patterns for GME by the International Zeolite Association as well as other literature sources.

TABLE 2

PXRD data (2-θ value) for CIT-9 compositions. See FIG. 3.

7.5 ± 0.1
11.6 ± 0.1
14.9 ± 0.1
17.9 ± 0.2
19.9 ± 0.1
21.75 ± 0.15
28.1 ± 0.2
30.1 ± 0.1

Thermogravimetric analysis of a typical air-dry as-made material (FIG. 4) showed that the total weight loss equaled about 20%. The weight loss fraction over 300° C. was attributed to the removal of the SDA and a good measure for the amount of its incorporation. Relative to the zeolite left at 900° C., the included amount of OSDA was found to be around 14 wt %, pointing to 1.4 OSDA molecules per unit cell.

$^{13}$C CP-MAS NMR was performed (FIG. 5) to further verify the OSDA was included in the zeolite. The NMR trace of the occluded carbon in the zeolite matched well with the OSDA standard (liquid dilution in water, measured in $^{13}$C CP-MAS). The assignments given in FIG. 5 were verified by liquid phase $^{13}$C NMR (not shown).

The CIT-9 material was not stable when calcined at 580° C. It seemed to transform into an AFI type molecular sieve. The instability of GME has been reported previously. To avoid this issue, the OSDA was removed via an ozone-treatment at 150° C. The materials retained their crystalline GME PXRD patterns as seen in FIG. 6 and FIG. 7 for MDU80 and MDU93 respectively.

The as-synthesized CIT-9 could also be calcined in presence of salts, as an alternative to the ozone-treatment for removal of the OSDA and preservation of the GME structure. An exemplary synthesis included mixing as-made CIT-9 (MDU80 recipe) with a 2M KCl solution, in a 1:2 zeolite:solution ratio. The slurry was then calcined using following thermal program: heating from room temperature to 90° C. at a rate of 0.1° C./min, then to 500° C. at a rate of 0.5° C./min, then isothermal for 5 h at 500° C. The structural features of GME, as witnessed by the upper trace in PXRD in FIG. 13, were still present after the treatment. If CIT-9 was calcined without using the salt solution, the PXRD trace changed in some places and was more resemblant of an AFI topology (see FIG. 13, middle trace): compared to GME, at 11.6 degrees 2-theta, a reflection disappeared while at 21.1 degrees 2-theta an additional signal appears (dotted indication squares). Similar GME preservation results were obtained with a 1M KCl solution (using a 1:4 zeolite:solution ratio) and with 2M NaCl.

Figure 6:
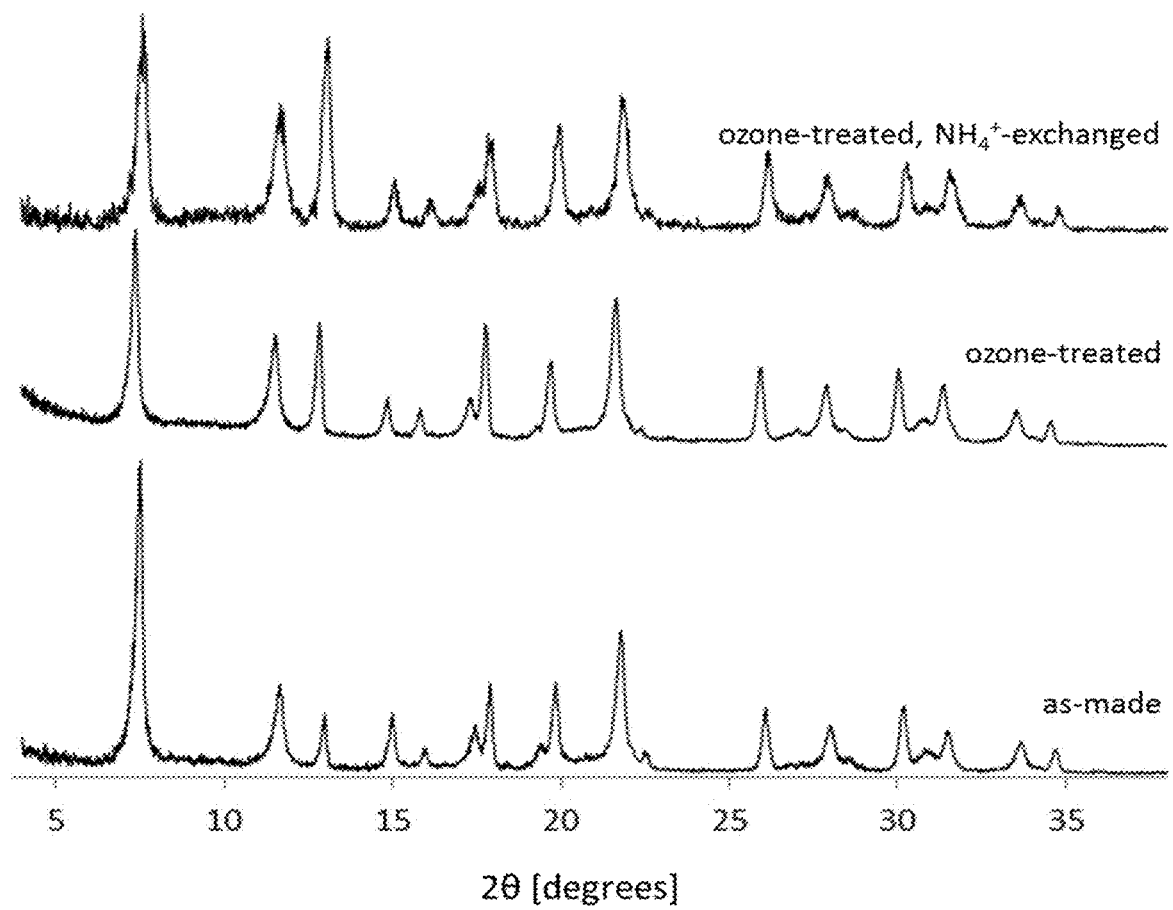
FIG. 6 shows PXRD traces of CIT-9 produced in synthesis MDU80: as made; after ozone-treatment; after ozone-treatment and subsequent NW-exchange.
Figure 7:
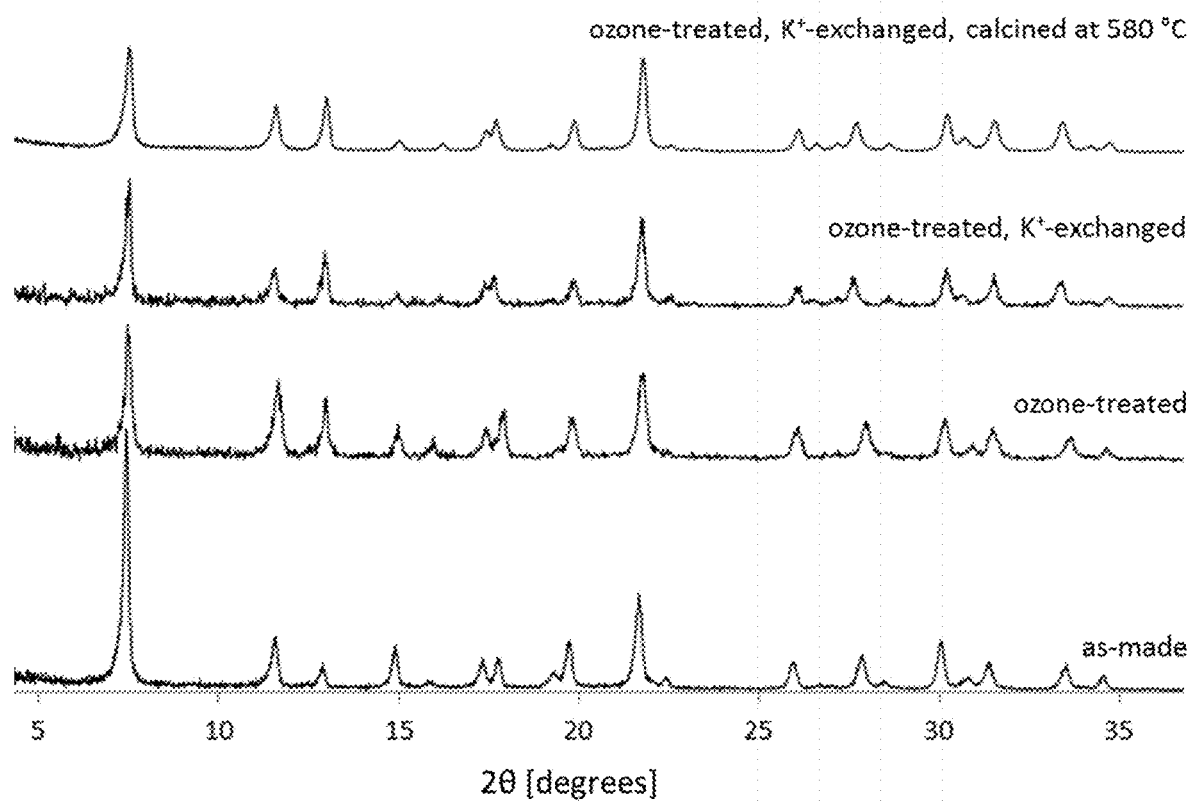
FIG. 7 shows PXRD traces of CIT-9 produced in synthesis MDU93: as made; after ozone-treatment; after ozone and subsequent K$^+$-exchange; after ozone, K$^+$-exchange and calcination at 580° C.

After ozone-treatment, the material was easily exchanged following state-of-the-art ion exchange protocols, e.g. with ammonium as demonstrated for MDU80 in FIG. 6 and with potassium, as demonstrated for MDU93 in FIG. 7. Furthermore, the K$^+$-CIT-9 was found to be very thermally stable, due to the stabilizing presence of the K$^+$ ions. This can be evidenced from the upper PXRD trace in FIG. 7, after calcination at 580° C.

Figure 8:
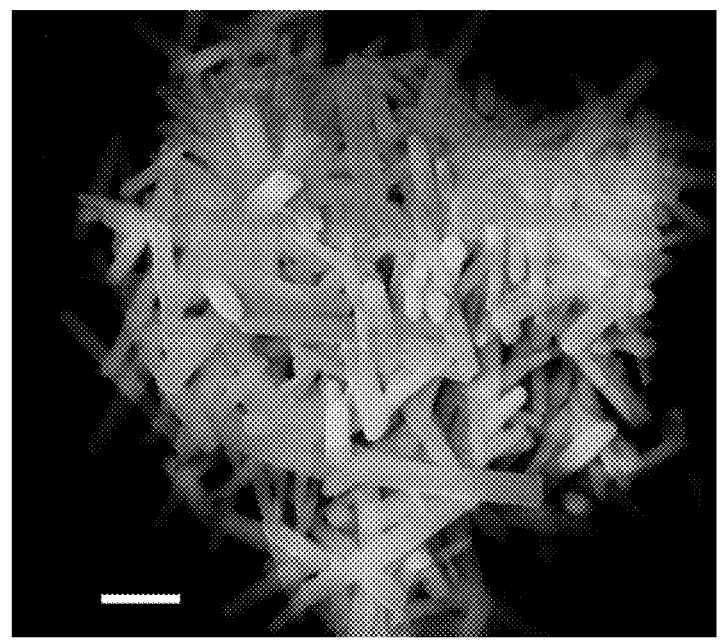
FIG. 8 shows SEM images of as-made CIT-9 produced in Table 1 entry 1: MDU80. 30,000× magnification. Bar=1 micron
Figure 9:
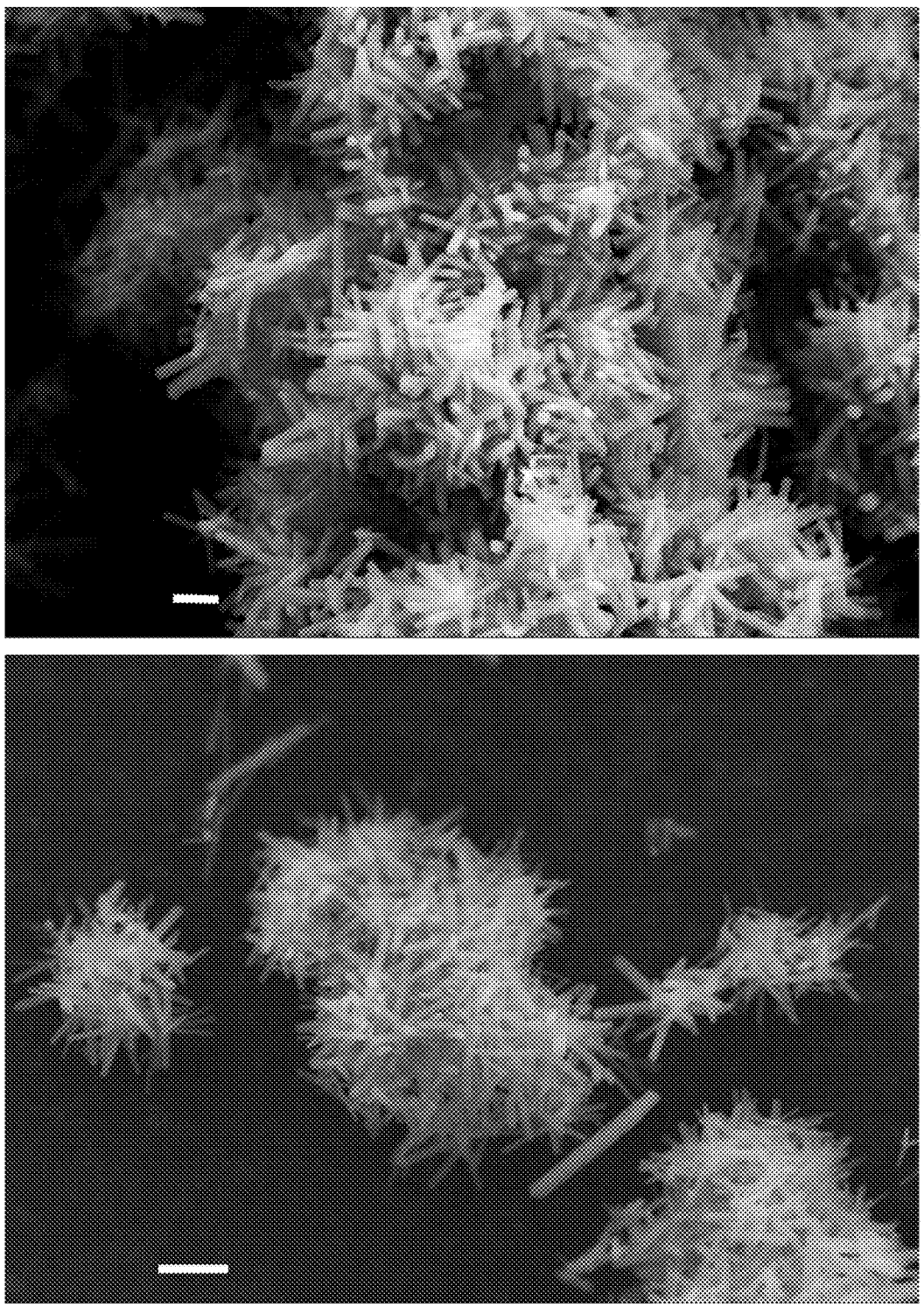
FIG. 9 shows SEM images of CIT-9 produced in Table 1 entry 2: MDU93. Upper: As-made material (16,030× magnification, Bar=1 micron); Bottom: After ozone-treatment, K$^+$-exchange and calcination at 580° C. (12,300× magnification, Bar=2 micron).

The morphology of the new material was further studied by SEM. Rectangular (coffin-shaped—to needle like) crystals with lengths of about 1-3 µm were obtained and observed (see, e.g., FIGS. 8 and 9).

The pore volumes of two CIT-9 materials were assessed by measuring the N$_2$- and Ar-physisorption isotherms after OSDA removal by ozone-treatment (FIG. 10). Both MDU53, probed by N$_2$, and MDU80, probed by Argon, showed promising sorption capacities. The pore volumes by t-plot analysis on the adsorption branch were 0.156 cm$^3$/g for MDU53 and 0.151 cm$^3$/g for MDU80. It should be noted that MDU53 had a significant ANA impurity in PXRD (the material after 110 h of synthesis was measured). This dense phase however does not possess sorption capacity. These high sorption capacities together with the absence of CHA signals in PXRD indicate that CIT-9 is an aluminosilicate of the GME topology with very little faulting and good pore volumes for applications in sorption and catalysis.

$^{27}$Al MAS NMR (FIG. 11) and $^{29}$Si MAS NMR (FIG. 12) were both used to further corroborate the successful synthesis of the aluminosilicate framework of CIT-9 (both measured on the calcined K-exchanged MDU93 sample). The absence of signals at 0 ppm in Al NMR and the presence of the large signal at 57 ppm showed that all aluminum was incorporated tetrahedrally into the framework. The Si NMR shows three characteristic signals of typical aluminosilicate materials with intermediate Al content. The intensities of these resonances at −98 ppm, 105 ppm and 110 ppm allow to calculate the Si/Al ratio according to the known formula. This led to a calculated Si/Al value of 3.95, well in accord with the Si/Al ratio of Table 1.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

All of the references cited in this disclosure are incorporated by reference herein in their entireties for all purposes.

What is claimed:

1. A crystalline microporous aluminosilicate composition of GME topology comprising:
    (a) an oxide of silicon, and optionally an oxide of germanium;
    (b) an oxide of aluminum, and optionally one or more oxides of boron, gallium, hafnium, iron, tin, titanium, indium, vanadium, or zirconium, wherein the molar ratio of the metals of (a) to the metals of (b) is from 4 to 4.2; and which crystalline microporous aluminosilicate composition of GME topology exhibits a powder XRD pattern having peaks having 2-theta values at 7.5+0.10, 11.6+0.10, 14.9+0.10, 17.9+0.2°, 19.9+0.1°, 21.75+0.15°, 28.1+0.20°, and 30.1+0.10, wherein the crystalline microporous aluminosilicate composition has pores that contain at least one isomer of the quaternary piperidinium cation of Formula (I):

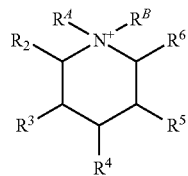

(I)

wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl; and the quaternary piperidinium cation has an associated bromide, chloride, fluoride, iodide nitrate, or hydroxide anion.

Figure 5:
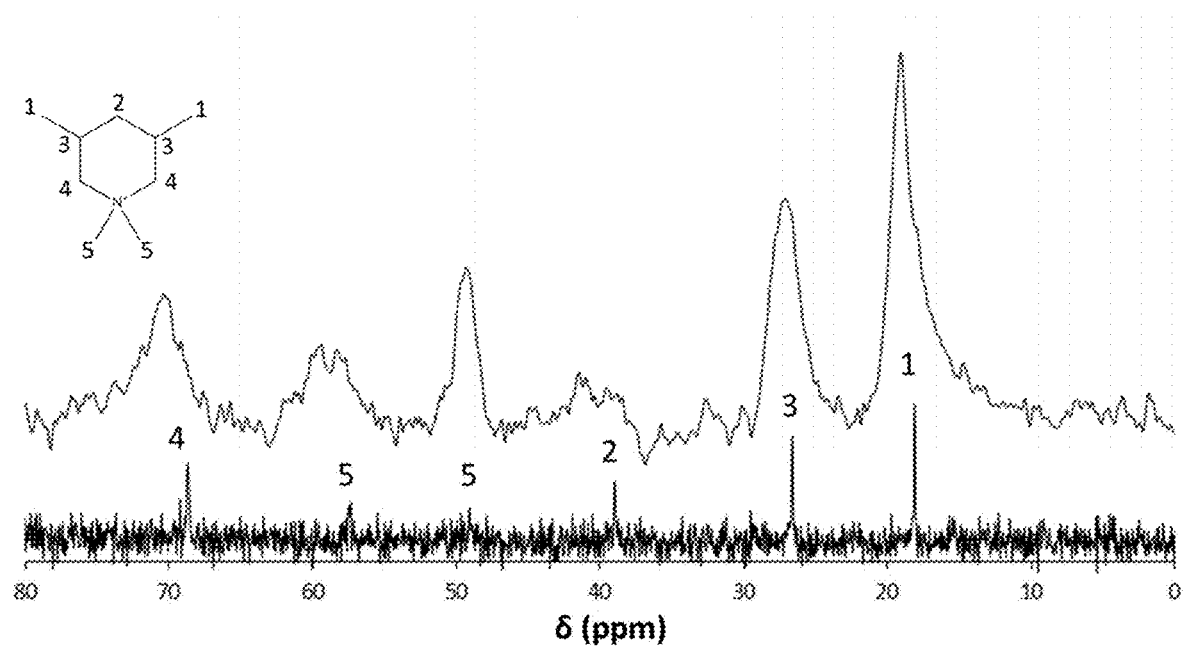
FIG. 5 shows $^{13}$C CP MAS NMR spectra of as-made MDU190 (upper trace) and the OSDA tetramethyl-N,N,3,5-piperidinium hydroxide (lower trace) (500 MHz).
Figure 13:
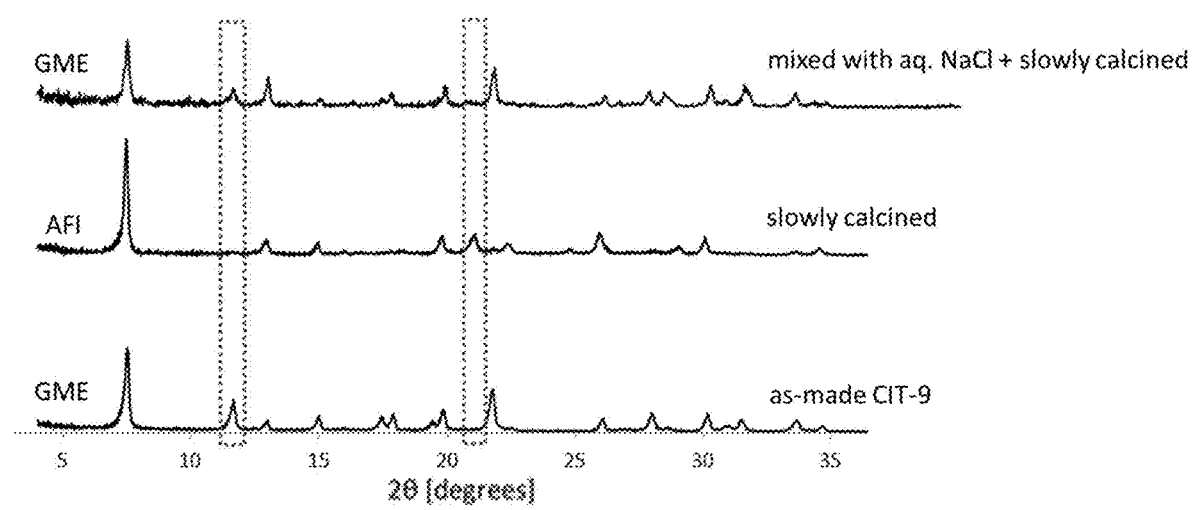
FIG. 13 shows PXRD patterns of as-made CIT-9, CIT-9 after calcination and CIT-9 after calcination in the presence of salt.

2. The crystalline microporous aluminosilicate composition of claim 1, that exhibits one or more of:

(a) an XRD diffraction pattern that is the same as or consistent with any one of those shown in FIG. 3, FIG. 6, FIG. 7, or FIG. 13;

(b) an $^{29}$Si MAS spectrum having a plurality of chemical shifts of about −99.1, −104.9 and −110.5 ppm, downfield of a peak corresponding to an external standard of tetramethylsilane;

(c) an $^{29}$Si MAS spectrum that is the same as or consistent with the one shown in FIG. 13;

(d) an $^{27}$Al MAS NMR spectrum that is the same as or consistent with the one shown in FIG. 11, or (e) a thermogravimetric analysis curve that is the same as or consistent with the one in FIG. 4; or (f) a $^{13}$C CP MAS NMR spectrum that is the same as or consistent with the one shown in FIG. 5.

3. The crystalline microporous aluminosilicate composition of claim 1, wherein the at least one isomer of the quaternary piperidinium cation of Formula (I) comprises at least one isomer of the quaternary piperidinium cation of Formula (IA) or (IB):

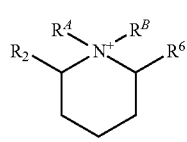

(IA)

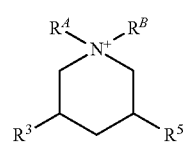

(IB)

wherein $R^2$, $R^3$, $R^5$, and $R^6$ are independently $C_{1-3}$ alkyl.

4. The crystalline microporous aluminosilicate composition of claim 1, wherein the at least one isomer of the quaternary piperidinium cation of Formula (I) comprises an N,N-dialkyl-2,6-lupetidinium cation or N,N-dialkyl-3,5-lupetidinium cation:

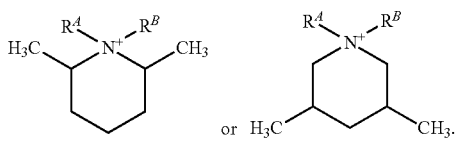

5. The crystalline microporous aluminosilicate composition of claim 1, wherein the at least one isomer of the quaternary piperidinium cation of Formula (I) comprises cis-N,N-dimethyl-3,5-lupetidinium cation, trans-N,N-dimethyl-3,5-lupetidinium cation, cis-N,N-dimethyl-2,6-lupetidinium cation, trans-N,N-dimethyl-2,6-lupetidinium cation or a combination thereof.

6. The crystalline microporous aluminosilicate composition of claim 1, prepared by a process comprising hydrothermally treating an aqueous composition comprising:

(a) a source of a silicon oxide, and optionally a source of germanium oxide, or combination thereof, wherein the source of silicon oxide is an aluminosilicate, a silicate, a silica hydrogel, amorphous silica, silicic acid, fumed silica, colloidal silica, tetra-alkyl orthosilicate, a silica hydroxide, silicon alkoxide, or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof, wherein the source of aluminum oxide is an alkoxide, hydroxide, or oxide of aluminum, a sodium aluminate, an aluminum siloxide, an aluminosilicate, or combination thereof;

(c) a mineralizing agent comprising an aqueous hydroxide;

(d) an organic structure directing agent (OSDA) comprising at least one isomer of the quaternary piperidinium cation of Formula (I):

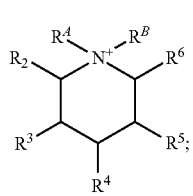

(I)

and (e) water;

under conditions to crystallize the crystalline microporous solid of GME topology containing the at least one isomer of the quaternary piperidinium cation of Formula (I);

wherein $R^A$ and $R^B$ are independently a $C_{1-3}$ alkyl, or together with the N to which they are bound form a 5 or 6 membered saturated or unsaturated ring; and $R^2$, $R^4$, and $R^6$ are H and $R^3$ and $R^5$ are cis-positioned $C_{1-3}$ alkyl; wherein
the quaternary piperidinium cation has an associated bromide, chloride, fluoride, iodide nitrate, or hydroxide anion.

7. The crystalline microporous aluminosilicate composition of claim 6, wherein the OSDA comprises at least one isomer of the quaternary piperidinium cation of Formula (IB):

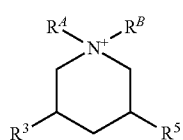
(IB)

wherein $R^3$ and $R^5$ are independently $C_{1-3}$ alkyl.

8. The crystalline microporous aluminosilicate composition of claim 6, wherein the quaternary piperidinium cation of Formula (I) comprises a cis-N,N-dialkyl-3,5-lupetidinium cation:

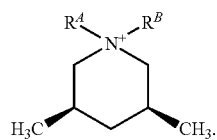

9. The crystalline microporous aluminosilicate composition of claim 6, wherein the quaternary piperidinium cation of Formula (I) comprises cis-N,N-dimethyl-3,5-lupetidinium cation

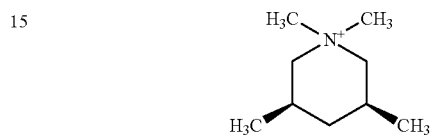

and the associated anion is hydroxide.

* * * * *